(12) United States Patent
Piletz et al.

(10) Patent No.: US 6,881,826 B1
(45) Date of Patent: Apr. 19, 2005

(54) IMIDAZOLINE RECEPTIVE POLYPEPTIDES

(75) Inventors: John E. Piletz, Madison, MS (US); Tina R. Ivanov, Manchester (GB)

(73) Assignee: The University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 09/414,643

(22) Filed: Oct. 8, 1999

Related U.S. Application Data

(60) Division of application No. 08/922,635, filed on Sep. 3, 1997, now Pat. No. 6,033,871, which is a continuation-in-part of application No. 08/650,766, filed on May 20, 1996, now Pat. No. 6,015,690.
(60) Provisional application No. 60/012,600, filed on Mar. 1, 1996.

(51) Int. Cl.[7] ............................................. C07K 14/705
(52) U.S. Cl. ..................................................... 530/350
(58) Field of Search ........................................ 530/350

(56) References Cited

PUBLICATIONS

George et al., Macromolecular sequencing and synthesis, Alan Riss , p. 127–149, 1988.*
EST04033, in : Adams et al., Nature Genet.4:256–67, 1993.*
P. Ernsberger et al., "Role of Imidazole Receptors in the Vasodepressor Response to Clonidine Analogs in the Rostral Ventrolateral Medulla[1]", The Journal of Pharmacology and Experimental Therapeutics vol. 253, No. 1, pp. 408–418, (1990).
J. Piletz et al., "Nonadrenergic Imidazoline Binding Sites on Human Platelets", The Journal of Pharmacology and Experimental Therapeutics, vol. 267, No. 3, pp. 1493–1502, (1993).
B. Lanier et al., "Structural and Ligand Recognition Properties of Imidazoline Binding Proteins in Tissues of Rat and Rabbit", The American Society for Pharmacology and Experimental Therapeutics, vol. 48, pp. 703–710, (1995).
F. Bennai et al., "Antiidiotypic Antibodies as Tools to Study Imidazoline Receptors", Annals New York Academy of Sciences, vol. 763, pp. 140–148, (1995).
H. Wang et al., "Isolation and Characterization of Imidazoline Receptor Protein from Bovine Adrenal Chromaffin Cells", The American Society for Pharmacology and Experimental Therapeutics, vol. 42, pp. 792–801, ((1992).
H. Wang et al. "Production and Characterization of Antibodies Specific for the Imidazoline Receptor Protein", The American Society for Pharmacology and Experimental Therapeutics, vol. 43, pp. 509–515, (1993).
P. Ernsberger et al., "I[1]–Imidazoline Receptors Definition, Characterization, Distribution, and Transmembrane Signaling", Annals New York Academy of Sciences, vol. 763, pp. 22–42, (1995).
Fourth IBRO Congress of Neuroscience, incomplete.
J. Piletz et al., "Imidazoline Receptors in Depression", American College of Neuropsychopharmacology, 34th Annual Meeting, p. 119, (1995).
A. Parini et al., "The Elusive Family of Imidazoline Binding Sites", TiPS, vol. 17, pp. 13–16, (1996).
J. Piletz et al., "Desipramine Lowers Tritiated Para–Aminoclonidine Binding in Platelets of Depressed Patients", Arch Gen Psychiatry, vol. 48, pp. 813–820, (1991).
J. Piletz et al., "Psychopharmacology of Imidazoline and $\alpha_2$–Adrenergic Receptors: Implications for Depression", Critical Reviews in Neurobiology, vol. 9, No. 1, pp. 29–66, (1994).
Lin, et al., Science 190:61–63 (1975).

* cited by examiner

*Primary Examiner*—Lorraine Spector
*Assistant Examiner*—Eliane Lazar-Wesley
(74) *Attorney, Agent, or Firm*—Crowell & Moring LLP

(57) ABSTRACT

A genomic DNA encoding a human imidazoline receptor is described. cDNAs encoding the receptor and fragments thereof are also provided. An amino acid sequence predicted to be 120,000 MW for nearly the entire protein is identified, as well as a middle fragment believed to contain the imidazoline binding site of the receptor. The protein is highly unique in its sequence and may represent the first in a novel family of receptor proteins. Methods of cloning the cDNA and expressing the imidazoline receptor in a host cell are described. Methods of preparing antibodies against the transfected protein are also described. Also, a screening method for identifying additional subtypes of this receptor are identified. Also, screening methods for identifying drugs that interact with the imidazoline receptor are described.

6 Claims, 6 Drawing Sheets

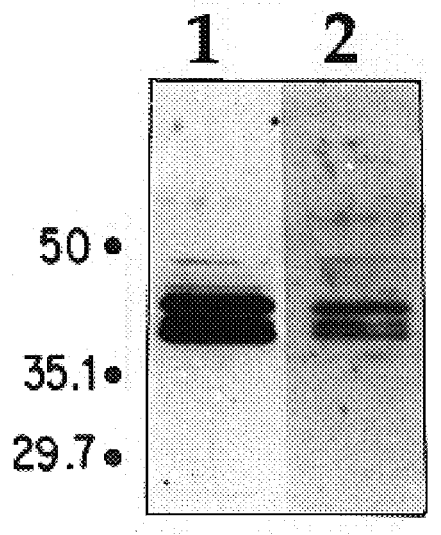
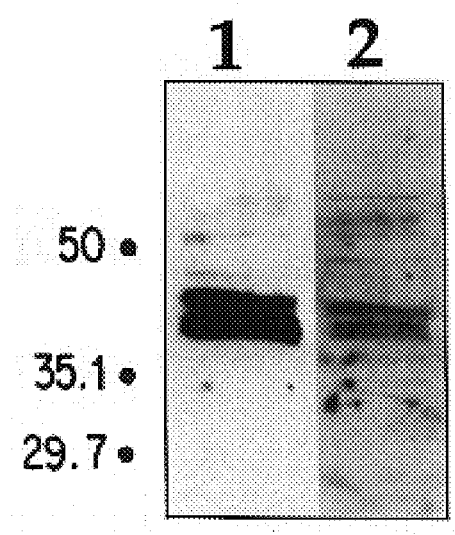
FIG. 1A  FIG. 1B
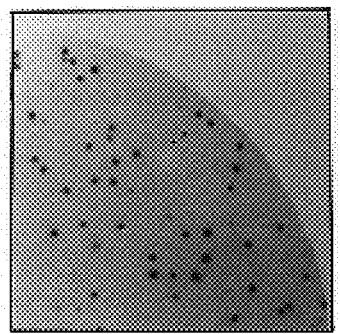
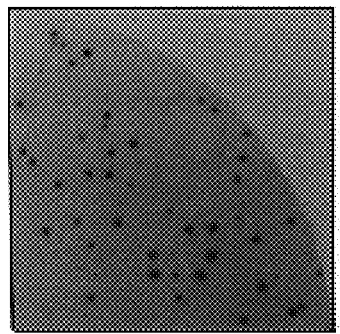
| REIS AB 1:15,000 DILUTION | DONTEWILL AB 1:20,000 DILUTION |
FIG. 2A  FIG. 2B

SEQUENCE LISTING

```
<160> NUMBER OF SEQ ID NOS: 22

<210> SEQ ID NO 1
<211> LENGTH: 3385
<212> TYPE: DNA
<213> ORGANISM: Homo sapiens
<220> FEATURE:
<221> NAME/KEY: CDS
<222> LOCATION: (1398)..(3383)

<400> SEQUENCE: 1
gctctagaac tagtggatcc cccgggctgc aggaattcca gtttaatact aaccctaatg      60
tgtgactgcg gtttacaaag agctctgtat caccctgggat agctttcagt agcaattcac    120
tacaactggt cctaaaaaat aataacaata ataataataa ttagagaatt aaaacccaac    180
agcatgttga atggttaaaa tcacgtaaga actgaaattt ggggtgggg tgtcctcaac    240 agctgagctt gtcctagcag tgaaaatgct cgcctccaag cagggctcag aaaggtctgg    300
agccctccag gcagagggct gagctcaggg ggctcttgga ggacactcac cccatggtcc    360
atgggatgct tctggcttcc ttaaaaacag ttgggcatcc gcattgtata agtaggtgga    420
gaccctagtg tggttctttt gaaggatatg ggaagggagg atgacgaact agagaagtgg    480
gaggggacca aaatcactga ggtcccagaa tatcatagat ttgggtatag gattggggtc    540
actaagaatt gagcaccagg aattccagct tcttcccatt aaagaaactg ggactggttt    600
tgccttggag gcctatgtag tgttttctgc ccctgtccca taccaagtct cattgatatt    660
tctgcagaat atcagatgaa aatctatttc taaagaccat tgggagaatg ggtggtggag    720
aaggagttgg agtggggttg ggggcagtt aaaaatgaat aaaaatctct cagctacaga    780
acccaaacat cacttccctc cgcattcaca gcatttccca gcagtcccca gatggttgtt    840
tccgtgggga cacagcagct gcctcatttc ccttcaggcc ccatgggctg ctggtcaacc    900
```

-continued

```
tcaggatcta ctaaagatga cgcaaatgcc gactgaacaa tctgaaaccc aaaggactcg    960
aggagagaca tgttctgctg aggagagaaa ggtgagccaa gggcagggcc caggtccccc   1020
aggggggccc cgagagcccg acatgcacc ttctggatgt gtttgttcaa gtaggactta   1080
gagcggaaga agctcccaca ttcagggcat gggtacttct tctccccatc agactccatt   1140 ttgttttttgg ggactgccat gtcgcaggag aaagagccat tggcactctg cttctctggc   1200
gtcttcaggt cgctggcatc tgagaggtca ccataggagt cagagctctc aatcggatcc   1260
tgatgtgagc atttctggcc ttctcggtta cagatactgc agaagttgct gggcccctcg   1320
ctgtgcttct tcaggtggtc tgccatgtat gctgcccgca agtacttccc acacacctgg   1380
cagggcacct tgtcttc atg aca ggc cag gtg gga gcg cag acg gtc tcg     1430
              Met Thr Gly Gln Val Gly Ala Gln Thr Val Ser
                1           5                  10 ggt ggc aaa aga agc att gca ggt ctg aca ctt gtg agg ccg ctc aga    1478
Gly Gly Lys Arg Ser Ile Ala Gly Leu Thr Leu Val Arg Pro Leu Arg
            15                  20                  25 agt gtg cac ctg ctt gat atg tcc gtt caa gtg atc agg cct gga gaa    1526
Ser Val His Leu Leu Asp Met Ser Val Gln Val Ile Arg Pro Gly Glu
        30                  35                  40 gcc ttt ccc aca gct ctg gca gat gta agg cgg aat tcc cca gag aag    1574
Ala Phe Pro Thr Ala Leu Ala Asp Val Arg Arg Asn Ser Pro Glu Lys
    45                  50                  55 aag ggt ggt gaa gac tcc cgg ctc tca gct gcc ccc tgc atc aga ccc    1622
Lys Gly Gly Glu Asp Ser Arg Leu Ser Ala Ala Pro Cys Ile Arg Pro
60                  65                  70                  75 agc agc tcc cct ccc act gtg gct ccc gca tct gcc tcc ctg ccc cag    1670
Ser Ser Ser Pro Pro Thr Val Ala Pro Ala Ser Ala Ser Leu Pro Gln
            80                  85                  90 ccc atc ctc tct aac caa gga atc atg ttc gtt cag gag gag gcc ctg    1718
Pro Ile Leu Ser Asn Gln Gly Ile Met Phe Val Gln Glu Glu Ala Leu
        95                  100                 105 gcc agc agc ctc tcg tcc act gac agt ctg act ccc gag cac cag ccc    1766
Ala Ser Ser Leu Ser Ser Thr Asp Ser Leu Thr Pro Glu His Gln Pro
    110                 115                 120 att gcc cag gga tgt tct gat tcc ttg gag tcc atc cct gcg gga cag    1814
Ile Ala Gln Gly Cys Ser Asp Ser Leu Glu Ser Ile Pro Ala Gly Gln
125                 130                 135 gca gct tcc gat gat tta agg gac gtg cca gga gct gtt ggt ggt gca    1862
Ala Ala Ser Asp Asp Leu Arg Asp Val Pro Gly Ala Val Gly Gly Ala
140                 145                 150                 155 agc cca gaa cat gcc gag ccg gag gtc cag gtg gtg ccg ggg tct ggc    1910
Ser Pro Glu His Ala Glu Pro Glu Val Gln Val Val Pro Gly Ser Gly
            160                 165                 170 cag atc atc ttc ctg ccc ttc acc tgc att ggc tac acg gcc acc aat    1958
Gln Ile Ile Phe Leu Pro Phe Thr Cys Ile Gly Tyr Thr Ala Thr Asn
        175                 180                 185 cag gac ttc atc cag cgc ctg agc aca ctg atc cgg cag gcc atc gag    2006
Gln Asp Phe Ile Gln Arg Leu Ser Thr Leu Ile Arg Gln Ala Ile Glu
    190                 195                 200 cgg cag ctg cct gcc tgg atc gag gct gcc aac cag cgg gag gag ggc    2054
Arg Gln Leu Pro Ala Trp Ile Glu Ala Ala Asn Gln Arg Glu Glu Gly
205                 210                 215 cag ggt gaa cag ggc gag gag gag gat gag gag gag gaa gaa gag gag    2102
Gln Gly Glu Gln Gly Glu Glu Glu Asp Glu Glu Glu Glu Glu Glu Glu
220                 225                 230                 235 gac gtg gct gag aac cgc tac ttt gaa atg ggg ccc cca gac gtg gag    2150
Asp Val Ala Glu Asn Arg Tyr Phe Glu Met Gly Pro Pro Asp Val Glu
                240                 245                 250
```

-continued

| | |
|---|---|
| gag gag gag gga gga ggc cag ggg gag gaa gag gag gag gaa gag gag<br>Glu Glu Glu Gly Gly Gly Gln Gly Glu Glu Glu Glu Glu Glu Glu Glu<br>              255                         260                      265 | 2198 |
| gat gaa gag gcc gag gag gag cgc ctg gct ctg gaa tgg gcc ctg ggc<br>Asp Glu Glu Ala Glu Glu Glu Arg Leu Ala Leu Glu Trp Ala Leu Gly<br>      270                        275                    280 | 2246 |
| gcg gac gag gac ttc ctg ctg gag cac atc cgc atc ctc aag gtg ctg<br>Ala Asp Glu Asp Phe Leu Leu Glu His Ile Arg Ile Leu Lys Val Leu<br>285                        290                    295 | 2294 |
| tgg tgc ttc ctg atc cat gtg cag ggc agt atc cgc cag ttc gcc gcc<br>Trp Cys Phe Leu Ile His Val Gln Gly Ser Ile Arg Gln Phe Ala Ala<br>300                        305                    310                    315 | 2342 |
| tgc ctt gtg ctc acc gac ttc ggc atc gca gtc ttc gag atc ccg cac<br>Cys Leu Val Leu Thr Asp Phe Gly Ile Ala Val Phe Glu Ile Pro His<br>                    320                    325                    330 | 2390 |
| cag gag tct cgg ggc agc agc cag cac atc ctc tcc tcc ctg cgc ttt<br>Gln Glu Ser Arg Gly Ser Ser Gln His Ile Leu Ser Ser Leu Arg Phe<br>              335                    340                    345 | 2438 |
| gtc ttt tgc ttc ccg cat ggc gac ctc acc gag ttt ggc ttc ctc atg<br>Val Phe Cys Phe Pro His Gly Asp Leu Thr Glu Phe Gly Phe Leu Met<br>      350                        355                    360 | 2486 |
| ccg gag ctg tgt ctg gtg ctc aag gta cgg cac agt gag aac acg ctc<br>Pro Glu Leu Cys Leu Val Leu Lys Val Arg His Ser Glu Asn Thr Leu<br>365                        370                    375 | 2534 |
| ttc att atc tcg gac gcc gcc aac ctg cac gag ttc cac gcg gac ctg<br>Phe Ile Ile Ser Asp Ala Ala Asn Leu His Glu Phe His Ala Asp Leu<br>380                        385                    390                    395 | 2582 |
| cgc tca tgc ttt gca ccc cag cac atg gcc atg ctg tgt agc ccc atc<br>Arg Ser Cys Phe Ala Pro Gln His Met Ala Met Leu Cys Ser Pro Ile<br>                    400                    405                    410 | 2630 |
| ctc tac ggc agc cac acc agc ctg cag gag ttc ctg cgc cag ctg ctc<br>Leu Tyr Gly Ser His Thr Ser Leu Gln Glu Phe Leu Arg Gln Leu Leu<br>              415                    420                    425 | 2678 |
| acc ttc tac aag gtg gct ggc ggc tgc cag gag cgc agc cag ggc tgc<br>Thr Phe Tyr Lys Val Ala Gly Gly Cys Gln Glu Arg Ser Gln Gly Cys<br>      430                        435                    440 | 2726 |
| ttc ccc gtc tac ctg gtc tac agt gac aag cgc atg gtg cag acg gcc<br>Phe Pro Val Tyr Leu Val Tyr Ser Asp Lys Arg Met Val Gln Thr Ala<br>                    445                    450                    455 | 2774 |
| gcc ggg gac tac tca ggc aac atc gag tgg gcc agc tgc aca ctc tgt<br>Ala Gly Asp Tyr Ser Gly Asn Ile Glu Trp Ala Ser Cys Thr Leu Cys<br>460                        465                    470                    475 | 2822 |
| tca gcc gtg cgg cgc tcc tgc tgc gcg ccc tct gag gcc gtc aag tcc<br>Ser Ala Val Arg Arg Ser Cys Cys Ala Pro Ser Glu Ala Val Lys Ser<br>                    480                    485                    490 | 2870 |
| gcc gcc atc ccc tac tgg ctg ttg ctc acg ccc cag cac ctc aac gtc<br>Ala Ala Ile Pro Tyr Trp Leu Leu Leu Thr Pro Gln His Leu Asn Val<br>              495                    500                    505 | 2918 |
| atc aag gcc gac ttc aac ccc atg ccc aac cgt ggc acc cac aac tgt<br>Ile Lys Ala Asp Phe Asn Pro Met Pro Asn Arg Gly Thr His Asn Cys<br>          510                        515                    520 | 2966 |
| cgc aac cgc aac agc ttc aag ctc agc cgt gtg ccg ctc tcc acc gtg<br>Arg Asn Arg Asn Ser Phe Lys Leu Ser Arg Val Pro Leu Ser Thr Val<br>525                        530                    535 | 3014 |
| ctg ctg gac ccc aca cgc agc tgt acc cag cct cgg ggc gcc ttt gct<br>Leu Leu Asp Pro Thr Arg Ser Cys Thr Gln Pro Arg Gly Ala Phe Ala<br>540                        545                    550                    555 | 3062 |
| gat ggc cac gtg cta gag ctg ctc gtg ggg tac cgc ttt gtc act gcc<br>Asp Gly His Val Leu Glu Leu Leu Val Gly Tyr Arg Phe Val Thr Ala | 3110 |

-continued

| | | | | | | | | | | | | | | | | |
|---|---|---|---|---|---|---|---|---|---|---|---|---|---|---|---|---|
| | | | | 560 | | | | | 565 | | | | | 570 | | |
| atc | ttc | gtg | ctg | ccc | cac | gag | aag | ttc | cac | ttc | ctg | cgc | gtc | tac | aac | 3158 |
| Ile | Phe | Val | Leu | Pro | His | Glu | Lys | Phe | His | Phe | Leu | Arg | Val | Tyr | Asn | |
| | | | 575 | | | | | 580 | | | | | 585 | | | |
| cag | ctg | cgg | gcc | tcg | ctg | cag | gac | ctg | aag | act | gtg | gtc | atc | gcc | aag | 3206 |
| Gln | Leu | Arg | Ala | Ser | Leu | Gln | Asp | Leu | Lys | Thr | Val | Val | Ile | Ala | Lys | |
| | | | 590 | | | | | 595 | | | | | 600 | | | |
| acc | ccc | ggg | acg | gga | ggc | agc | ccc | cag | ggc | tcc | ttt | gcg | gat | ggc | cag | 3254 |
| Thr | Pro | Gly | Thr | Gly | Gly | Ser | Pro | Gln | Gly | Ser | Phe | Ala | Asp | Gly | Gln | |
| | 605 | | | | | 610 | | | | | 615 | | | | | |
| cct | gcc | gag | cgc | agg | gcc | agc | aat | gac | cag | cgt | ccc | cag | gag | gtc | cca | 3302 |
| Pro | Ala | Glu | Arg | Arg | Ala | Ser | Asn | Asp | Gln | Arg | Pro | Gln | Glu | Val | Pro | |
| 620 | | | | | 625 | | | | | 630 | | | | | 635 | |
| gca | gag | gct | ctg | gcc | ccg | gcc | cca | gtg | gaa | gtc | cca | gct | cca | gcc | ccg | 3350 |
| Ala | Glu | Ala | Leu | Ala | Pro | Ala | Pro | Val | Glu | Val | Pro | Ala | Pro | Ala | Pro | |
| | | | | 640 | | | | | 645 | | | | | 650 | | |
| gaa | ttc | gat | atc | aag | ctt | atc | gat | acc | gtc | gac | ct | | | | | 3385 |
| Glu | Phe | Asp | Ile | Lys | Leu | Ile | Asp | Thr | Val | Asp | | | | | | |
| | | | 655 | | | | | 660 | | | | | | | | |

<210> SEQ ID NO 2
<211> LENGTH: 1954
<212> TYPE: DNA
<213> ORGANISM: Homo sapiens

<400> SEQUENCE: 2

```
atgacaggcc aggtgggagc gcagacggtc tcgggtggca aaagaagcat tgcaggtctg      60
acacttgtga ggccgctcag aagtgtgcac ctgcttgata tgtccgttca agtgatcagg     120
cctggagaag cctttcccac agctctggca gatgtaaggc ggaattcccc agagaagaag     180
ggtggtgaag actcccggct ctcagctgcc cctgcatca gacccagcag ctcccctccc      240
actgtggctc ccgcatctgc ctccctgccc cagcccatcc tctctaacca aggaatcatg     300
ttcgttcagg aggaggccct ggccagcagc ctctcgtcca ctgacagtct gactcccgag     360
caccagccca ttgcccaggg atgttctgat tccttggagt ccatccctgc gggacaggca     420
gcttccgatg atttaaggga cgtgccagga gctgttggtg gtgcaagccc agaacatgcc     480
gagccggagg tccaggtggt gccggggtct ggccagatca tcttcctgcc cttcacctgc     540
attggctaca cggccaccaa tcaggacttc atccagcgcc tgagcacact gatccggcag     600
gccatcgagc ggcagctgcc tgcctggatc gaggctgcca accagcggga ggagggccag     660
ggtgaacagg gcgaggagga ggatgaggag gaggaagaag aggaggacgt ggctgagaac     720
cgctactttg aaatgggggcc cccagacgtg gaggaggagg agggaggagg ccaggggggag     780
gaagaggagg aggaagagga ggatgaagag gccgaggagg agcgcctggc tctggaatgg     840
gccctgggcg cggacgagga cttcctgctg gagcacatcc gcatcctcaa ggtgctgtgg     900
tgcttcctga tccatgtgca gggcagtatc cgccagttcg ccgcctgcct tgtgctcacc     960
gacttcggca tcgcagtctt cgagatcccg caccaggagt ctcggggcag cagccagcac    1020
atcctctcct ccctgcgctt tgtcttttgc ttcccgcatg cgacctcac cgagtttggc     1080
ttcctcatgc cggagctgtg tctggtgctc aaggtacggc acagtgagaa cacgctcttc    1140
attatctcgg acgccgccaa cctgcacgag ttccacgcgg acctgcgctc atgctttgca    1200
ccccagcaca tggccatgct gtgtagcccc atcctctacg gcagccacac cagcctgcag    1260
gagttcctgc gccagctgct caccttctac aaggtggctg cggctgcca ggagcgcagc    1320
cagggctgct tccccgtcta cctggtctac agtgacaagc gcatggtgca gacggccgcc    1380
```

-continued

```
ggggactact caggcaacat cgagtgggcc agctgcacac tctgttcagc cgtgcggcgc    1440
tcctgctgcg cgccctctga ggccgtcaag tccgccgcca tccctactg gctgttgctc     1500 acgccccagc acctcaacgt catcaaggcc gacttcaacc ccatgcccaa ccgtggcacc    1560
cacaactgtc gcaaccgcaa cagcttcaag ctcagccgtg tgccgctctc caccgtgctg    1620
ctggacccca cacgcagctg tacccagcct cggggcgcct ttgctgatgg ccacgtgcta    1680
gagctgctcg tggggtaccg ctttgtcact gccatcttcg tgctgcccca cgagaagttc    1740
cacttcctgc gcgtctacaa ccagctgcgg gcctcgctgc aggacctgaa gactgtggtc    1800
atcgccaaga ccccggac gggaggcagc ccccagggct cctttgcgga tggccagcct      1860
gccgagcgca gggccagcaa tgaccagcgt ccccaggagg tcccagcaga ggctctggcc    1920
ccggccccag tggaagtccc agctccagcc ccgg                                1954
```

<210> SEQ ID NO 3
<211> LENGTH: 3318
<212> TYPE: DNA
<213> ORGANISM: Homo sapiens

<400> SEQUENCE: 3

```
aattccagtt taatactaac cctaatgtgt gactgcggtt tacaaagagc tctgtatcac     60
ctgggatagc tttcagtagc aattcactac aactggtcct aaaaaataat aacaataata   120
ataataatta gagaattaaa acccaacagc atgttgaatg gttaaaatca cgtaagaact   180
gaaatttggg gtgggggtgt cctcaacagc tgagcttgtc ctagcagtga aaatgctcgc   240
ctccaagcag ggctcagaaa ggtctggagc cctccaggca gagggctgag ctcaggggc    300 tcttggagga cactcacccc atggtccatg ggatgcttct ggcttcctta aaaacagttg   360
ggcatccgca ttgtataagt aggtggagac cctagtgtgg ttcttttgaa ggatatggga   420
agggaggatg acgaactaga gaagtgggag gggaccaaaa tcactgaggt cccagaatat   480
catagatttg ggtataggat tggggtcact aagaattgag caccaggaat tccagcttct   540
tcccattaaa gaaactggga ctggttttgc cttggaggcc tatgtagtgt tttctgcccc   600
tgtcccatac caagtctcat tgatatttct gcagaatatc agatgaaaat ctatttctaa   660
agaccattgg gagaatgggt ggtggagaag gagttggagt ggggttgggg ggcagttaaa   720
aatgaataaa aatctctcag ctacagaacc caaacatcac ttccctccgc attcacagca   780
tttcccagca gtccccagat ggttgtttcc gtggggacac agcagctgcc tcatttccct   840
tcaggcccca tgggctgctg gtcaacctca ggatctacta aagatgacgc aaatgccgac   900
tgaacaatct gaaacccaaa ggactcgagg agagacatgt tctgctgagg agagaaaggt   960
gagccaaggg cagggcccag gtccccagg gggcccccga gagcccggac atgcaccttc    1020
tggatgtgtt tgttcaagta ggacttagag cggaagaagc tcccacattc agggcatggg   1080
tacttcttct ccccatcaga ctccatttg ttttgggga ctgccatgtc gcaggagaaa     1140
gagccattgg cactctgctt ctctggcgtc ttcaggtcgc tggcatctga ggtcacca     1200 taggagtcag agctctcaat cggatcctga tgtgagcatt tctggccttc tcggttacag   1260
atactgcaga agttgctggg cccctcgctg tgcttcttca ggtggtctgc catgtatgct   1320
gcccgcaagt acttcccaca cacctggcag ggcaccttgt cttcatgaca ggccaggtgg   1380
gagcgcagac ggtctcgggt ggcaaaagaa gcattgcagg tctgacactt gtgaggccgc   1440
tcagaagtgt gcacctgctt gatatgtccg ttcaagtgat caggcctgga gaagcctttc   1500
```

```
ccacagctct ggcagatgta aggcggaatt ccccagagaa gaagggtggt gaagactccc    1560
ggctctcagc tgcccctgc atcagaccca gcagctcccc tcccactgtg gctcccgcat    1620
ctgcctccct gccccagccc atcctctcta accaaggaat catgttcgtt caggaggagg    1680
ccctggccag cagcctctcg tccactgaca gtctgactcc cgagcaccag cccattgccc    1740
agggatgttc tgattccttg gagtccatcc ctgcgggaca ggcagcttcc gatgatttaa    1800
gggacgtgcc aggagctgtt ggtggtgcaa gcccagaaca tgccgagccg gaggtccagg    1860
tggtgccggg gtctggccag atcatcttcc tgcccttcac ctgcattggc tacacggcca    1920
ccaatcagga cttcatccag cgcctgagca cactgatccg gcaggccatc gagcggcagc    1980
tgcctgcctg gatcgaggct gccaaccagc gggaggaggg ccagggtgaa cagggcgagg    2040
aggaggatga ggaggaggaa gaagaggagg acgtggctga gaaccgctac tttgaaatgg    2100
ggcccccaga cgtggaggag gaggagggag gaggccaggg ggaggaagag gaggaggaag    2160
aggaggatga agaggccgag gaggagcgcc tggctctgga atgggccctg ggcgcggacg    2220
aggacttcct gctggagcac atccgcatcc tcaaggtgct gtggtgcttc ctgatccatg    2280
tgcagggcag tatccgccag ttcgccgcct gccttgtgct caccgacttc ggcatcgcag    2340
tcttcgagat cccgcaccag gagtctcggg gcagcagcca gcacatcctc tcctccctgc    2400
gctttgtctt ttgcttcccg catggcgacc tcaccgagtt tggcttcctc atgccggagc    2460
tgtgtctggt gctcaaggta cggcacagtg agaacacgct cttcattatc tcggacgccg    2520
ccaacctgca cgagttccac gcggacctgc gctcatgctt tgcacccag cacatggcca    2580 tgctgtgtag ccccatcctc tacggcagcc acaccagcct gcaggagttc ctgcgccagc    2640
tgctcacctt ctacaaggtg gctggcggct gccaggagcg cagccagggc tgcttccccg    2700
tctacctggt ctacagtgac aagcgcatgg tgcagacggc cgccggggac tactcaggca    2760
acatcgagtg ggccagctgc acactctgtt cagccgtgcg gcgctcctgc tgcgcgccct    2820
ctgaggccgt caagtccgcc gccatccct actggctgtt gctcacgccc cagcacctca    2880
acgtcatcaa ggccgacttc aaccccatgc ccaaccgtgg cacccacaac tgtcgcaacc    2940
gcaacagctt caagctcagc cgtgtgccgc tctccaccgt gctgctggac cccacacgca    3000
gctgtaccca gcctcgggc gccttttgctg atggccacgt gctagagctg ctcgtggggt    3060
accgctttgt cactgccatc ttcgtgctgc cccacgagaa gttccacttc ctgcgcgtct    3120
acaaccagct gcgggcctcg ctgcaggacc tgaagactgt ggtcatcgcc aagacccccg    3180
ggacgggagg cagccccag ggctcctttg cggatggcca gcctgccgag cgcagggcca    3240
gcaatgacca cgtcccag gaggtcccag cagaggctct ggccccggcc ccagtggaag    3300
tcccagctcc agccccgg                                                  3318

<210> SEQ ID NO 4
<211> LENGTH: 1171
<212> TYPE: DNA
<213> ORGANISM: Homo sapiens

<400> SEQUENCE: 4
gaggaggagg aagaggagga tgaagaggcc gaggaggagc gcctggctct ggaatgggcc      60
ctgggcgcgg acgaggactt cctgctggag cacatccgca tcctcaaggt gctgtggtgc     120
ttcctgatcc atgtgcaggg cagtatccgc cagttcgccg cctgccttgt gctcaccgac     180
ttcggcatcg cagtcttcga gatcccgcac caggagtctc ggggcagcag ccagcacatc     240
ctctcctccc tgcgctttgt cttttgcttc ccgcatggcg acctcaccga gtttggcttc     300
```

-continued

```
ctcatgccgg agctgtgtct ggtgctcaag gtacggcaca gtgagaacac gctcttcatt      360
atctcggacg ccgccaacct gcacgagttc cacgcggacc tgcgctcatg ctttgcaccc      420
cagcacatgg ccatgctgtg tagccccatc ctctacggca ccacaccag cctgcaggag       480
ttcctgcgcc agctgctcac cttctacaag gtggctggcg gctgccagga gcgcagccag      540
ggctgcttcc ccgtctacct ggtctacagt gacaagcgca tggtgcagac ggccgccggg      600
gactactcag gcaacatcga gtgggccagc tgcacactct gttcagccgt gcggcgctcc      660
tgctgcgcgc cctctgaggc cgtcaagtcc gccgccatcc cctactggct gttgctcacg      720
ccccagcacc tcaacgtcat caaggccgac ttcaaccccea tgcccaaccg tgcacccac      780
aactgtcgca accgcaacag cttcaagctc agccgtgtgc cgctctccac cgtgctgctg      840
gaccccacac gcagctgtac ccagcctcgg ggcgcctttg ctgatggcca cgtgctagag      900
ctgctcgtgg ggtaccgctt tgtcactgcc atcttcgtgc tgccccacga aagttccac       960
ttcctgcgcg tctacaacca gctgcgggcc tcgctgcagg acctgaagac tgtggtcatc     1020
gccaagaccc ccgggacggg aggcagcccc cagggctcct tgcggatgg ccagcctgcc      1080
gagcgcaggg ccagcaatga ccagcgtccc caggaggtcc cagcagaggc tctggccccg     1140
gccccagtgg aagtcccagc tccagccccg g                                    1171
```

<210> SEQ ID NO 5
<211> LENGTH: 651
<212> TYPE: PRT
<213> ORGANISM: Homo sapiens

<400> SEQUENCE: 5

```
Met Thr Gly Gln Val Gly Ala Gln Thr Val Ser Gly Gly Lys Arg Ser
  1               5                  10                  15

Ile Ala Gly Leu Thr Leu Val Arg Pro Leu Arg Ser Val His Leu Leu
             20                  25                  30

Asp Met Ser Val Gln Val Ile Arg Pro Gly Glu Ala Phe Pro Thr Ala
         35                  40                  45

Leu Ala Asp Val Arg Arg Asn Ser Pro Glu Lys Lys Gly Gly Glu Asp
     50                  55                  60

Ser Arg Leu Ser Ala Ala Pro Cys Ile Arg Pro Ser Ser Ser Pro Pro
 65                  70                  75                  80

Thr Val Ala Pro Ala Ser Ala Ser Leu Pro Gln Pro Ile Leu Ser Asn
                 85                  90                  95

Gln Gly Ile Met Phe Val Gln Glu Glu Ala Leu Ala Ser Ser Leu Ser
            100                 105                 110

Ser Thr Asp Ser Leu Thr Pro Glu His Gln Pro Ile Ala Gln Gly Cys
        115                 120                 125

Ser Asp Ser Leu Glu Ser Ile Pro Ala Gly Gln Ala Ala Ser Asp Asp
    130                 135                 140

Leu Arg Asp Val Pro Gly Ala Val Gly Gly Ala Ser Pro Glu His Ala
145                 150                 155                 160

Glu Pro Glu Val Gln Val Val Pro Gly Ser Gly Gln Ile Ile Phe Leu
                165                 170                 175

Pro Phe Thr Cys Ile Gly Tyr Thr Ala Thr Asn Gln Asp Phe Ile Gln
            180                 185                 190

Arg Leu Ser Thr Leu Ile Arg Gln Ala Ile Glu Arg Gln Leu Pro Ala
        195                 200                 205

Trp Ile Glu Ala Ala Asn Gln Arg Glu Glu Gly Gln Gly Glu Gln Gly
```

-continued

```
                210                 215                 220
Glu Glu Glu Asp Glu Glu Glu Glu Glu Asp Val Ala Glu Asn
225                 230                 235                 240

Arg Tyr Phe Glu Met Gly Pro Pro Asp Val Glu Glu Glu Gly Gly
                245                 250                 255

Gly Gln Gly Glu Glu Glu Glu Glu Glu Asp Glu Glu Ala Glu
                260                 265                 270

Glu Glu Arg Leu Ala Leu Glu Trp Ala Leu Gly Ala Asp Glu Asp Phe
                275                 280                 285

Leu Leu Glu His Ile Arg Ile Leu Lys Val Leu Trp Cys Phe Leu Ile
                290                 295                 300

His Val Gln Gly Ser Ile Arg Gln Phe Ala Ala Cys Leu Val Leu Thr
305                 310                 315                 320

Asp Phe Gly Ile Ala Val Phe Glu Ile Pro His Gln Glu Ser Arg Gly
                325                 330                 335

Ser Ser Gln His Ile Leu Ser Ser Leu Arg Phe Val Phe Cys Phe Pro
                340                 345                 350

His Gly Asp Leu Thr Glu Phe Gly Phe Leu Met Pro Glu Leu Cys Leu
                355                 360                 365

Val Leu Lys Val Arg His Ser Glu Asn Thr Leu Phe Ile Ile Ser Asp
370                 375                 380

Ala Ala Asn Leu His Glu Phe His Ala Asp Leu Arg Ser Cys Phe Ala
385                 390                 395                 400

Pro Gln His Met Ala Met Leu Cys Ser Pro Ile Leu Tyr Gly Ser His
                405                 410                 415

Thr Ser Leu Gln Glu Phe Leu Arg Gln Leu Leu Thr Phe Tyr Lys Val
                420                 425                 430

Ala Gly Gly Cys Gln Glu Arg Ser Gln Gly Cys Phe Pro Val Tyr Leu
                435                 440                 445

Val Tyr Ser Asp Lys Arg Met Val Gln Thr Ala Ala Gly Asp Tyr Ser
                450                 455                 460

Gly Asn Ile Glu Trp Ala Ser Cys Thr Leu Cys Ser Ala Val Arg Arg
465                 470                 475                 480

Ser Cys Cys Ala Pro Ser Glu Ala Val Lys Ser Ala Ala Ile Pro Tyr
                485                 490                 495

Trp Leu Leu Leu Thr Pro Gln His Leu Asn Val Ile Lys Ala Asp Phe
                500                 505                 510

Asn Pro Met Pro Asn Arg Gly Thr His Asn Cys Arg Asn Arg Asn Ser
                515                 520                 525

Phe Lys Leu Ser Arg Val Pro Leu Ser Thr Val Leu Leu Asp Pro Thr
530                 535                 540

Arg Ser Cys Thr Gln Pro Arg Gly Ala Phe Ala Asp Gly His Val Leu
545                 550                 555                 560

Glu Leu Leu Val Gly Tyr Arg Phe Val Thr Ala Ile Phe Val Leu Pro
                565                 570                 575

His Glu Lys Phe His Phe Leu Arg Val Tyr Asn Gln Leu Arg Ala Ser
                580                 585                 590

Leu Gln Asp Leu Lys Thr Val Val Ile Ala Lys Thr Pro Gly Thr Gly
                595                 600                 605

Gly Ser Pro Gln Gly Ser Phe Ala Asp Gly Gln Pro Ala Glu Arg Arg
                610                 615                 620

Ala Ser Asn Asp Gln Arg Pro Gln Glu Val Pro Ala Glu Ala Leu Ala
625                 630                 635                 640
```

```
Pro Ala Pro Val Glu Val Pro Ala Pro Ala Pro
            645                 650

<210> SEQ ID NO 6
<211> LENGTH: 390
<212> TYPE: PRT
<213> ORGANISM: Homo sapiens

<400> SEQUENCE: 6

Glu Glu Glu Glu Glu Asp Glu Glu Ala Glu Glu Arg Leu Ala
 1               5                  10                  15

Leu Glu Trp Ala Leu Gly Ala Asp Glu Asp Phe Leu Leu Glu His Ile
             20                  25                  30

Arg Ile Leu Lys Val Leu Trp Cys Phe Leu Ile His Val Gln Gly Ser
             35                  40                  45

Ile Arg Gln Phe Ala Ala Cys Leu Val Leu Thr Asp Phe Gly Ile Ala
         50                  55                  60

Val Phe Glu Ile Pro His Gln Glu Ser Arg Gly Ser Ser Gln His Ile
 65                  70                  75                  80

Leu Ser Ser Leu Arg Phe Val Phe Cys Phe Pro His Gly Asp Leu Thr
                 85                  90                  95

Glu Phe Gly Phe Leu Met Pro Glu Leu Cys Leu Val Leu Lys Val Arg
            100                 105                 110

His Ser Glu Asn Thr Leu Phe Ile Ile Ser Asp Ala Ala Asn Leu His
            115                 120                 125

Glu Phe His Ala Asp Leu Arg Ser Cys Phe Ala Pro Gln His Met Ala
130                 135                 140

Met Leu Cys Ser Pro Ile Leu Tyr Gly Ser His Thr Ser Leu Gln Glu
145                 150                 155                 160

Phe Leu Arg Gln Leu Leu Thr Phe Tyr Lys Val Ala Gly Gly Cys Gln
                165                 170                 175

Glu Arg Ser Gln Gly Cys Phe Pro Val Tyr Leu Val Tyr Ser Asp Lys
            180                 185                 190

Arg Met Val Gln Thr Ala Ala Gly Asp Tyr Ser Gly Asn Ile Glu Trp
            195                 200                 205

Ala Ser Cys Thr Leu Cys Ser Ala Val Arg Arg Ser Cys Cys Ala Pro
210                 215                 220

Ser Glu Ala Val Lys Ser Ala Ala Ile Pro Tyr Trp Leu Leu Leu Thr
225                 230                 235                 240

Pro Gln His Leu Asn Val Ile Lys Ala Asp Phe Asn Pro Met Pro Asn
                245                 250                 255

Arg Gly Thr His Asn Cys Arg Asn Arg Asn Ser Phe Lys Leu Ser Arg
            260                 265                 270

Val Pro Leu Ser Thr Val Leu Leu Asp Pro Thr Arg Ser Cys Thr Gln
            275                 280                 285

Pro Arg Gly Ala Phe Ala Asp Gly His Val Leu Glu Leu Leu Val Gly
        290                 295                 300

Tyr Arg Phe Val Thr Ala Ile Phe Val Leu Pro His Glu Lys Phe His
305                 310                 315                 320

Phe Leu Arg Val Tyr Asn Gln Leu Arg Ala Ser Leu Gln Asp Leu Lys
                325                 330                 335

Thr Val Val Ile Ala Lys Thr Pro Gly Thr Gly Gly Ser Pro Gln Gly
            340                 345                 350

Ser Phe Ala Asp Gly Gln Pro Ala Glu Arg Arg Ala Ser Asn Asp Gln
```

-continued

```
                355                 360                 365
Arg Pro Gln Glu Val Pro Ala Glu Ala Leu Ala Pro Ala Pro Val Glu
    370                 375                 380
Val Pro Ala Pro Ala Pro
385                 390

<210> SEQ ID NO 7
<211> LENGTH: 20
<212> TYPE: DNA
<213> ORGANISM: Homo sapiens

<400> SEQUENCE: 7
cttgaggatg cggatgtgct                                               20

<210> SEQ ID NO 8
<211> LENGTH: 18
<212> TYPE: DNA
<213> ORGANISM: Homo sapiens

<400> SEQUENCE: 8
ccatggggtg agtgtcct                                                 18

<210> SEQ ID NO 9
<211> LENGTH: 18
<212> TYPE: DNA
<213> ORGANISM: Homo sapiens

<400> SEQUENCE: 9
aggacactca ccccatgg                                                 18

<210> SEQ ID NO 10
<211> LENGTH: 20
<212> TYPE: DNA
<213> ORGANISM: Homo sapiens

<400> SEQUENCE: 10
gtatgggaca ggggcagaaa                                               20

<210> SEQ ID NO 11
<211> LENGTH: 20
<212> TYPE: DNA
<213> ORGANISM: Homo sapiens

<400> SEQUENCE: 11
tttctaaaga ccattgggag                                               20

<210> SEQ ID NO 12
<211> LENGTH: 20
<212> TYPE: DNA
<213> ORGANISM: Homo sapiens

<400> SEQUENCE: 12
ccattttaaa gtagcggttc                                               20

<210> SEQ ID NO 13
<211> LENGTH: 20
<212> TYPE: DNA
<213> ORGANISM: Homo sapiens

<400> SEQUENCE: 13
aggagagaaa ggtgagccaa                                               20
```

```
<210> SEQ ID NO 14
<211> LENGTH: 20
<212> TYPE: DNA
<213> ORGANISM: Homo sapiens

<400> SEQUENCE: 14
gtagatcctg aggttgacca                                             20

<210> SEQ ID NO 15
<211> LENGTH: 20
<212> TYPE: DNA
<213> ORGANISM: Homo sapiens

<400> SEQUENCE: 15
tgtgagcatt tctggccttc                                             20

<210> SEQ ID NO 16
<211> LENGTH: 20
<212> TYPE: DNA
<213> ORGANISM: Homo sapiens

<400> SEQUENCE: 16
tgaagacgcc agagaagcag                                             20

<210> SEQ ID NO 17
<211> LENGTH: 20
<212> TYPE: DNA
<213> ORGANISM: Homo sapiens

<400> SEQUENCE: 17
gcctcacaag tgtcagacct                                             20

<210> SEQ ID NO 18
<211> LENGTH: 18
<212> TYPE: DNA
<213> ORGANISM: Homo sapiens

<400> SEQUENCE: 18
agaagggtgg tgaagact                                               18

<210> SEQ ID NO 19
<211> LENGTH: 20
<212> TYPE: DNA
<213> ORGANISM: Homo sapiens

<400> SEQUENCE: 19
cttggttaga gaggatgggc                                             20

<210> SEQ ID NO 20
<211> LENGTH: 20
<212> TYPE: DNA
<213> ORGANISM: Homo sapiens

<400> SEQUENCE: 20
gcccatcctc tctaaccaag                                             20

<210> SEQ ID NO 21
<211> LENGTH: 15202
<212> TYPE: DNA
<213> ORGANISM: Homo sapiens

<400> SEQUENCE: 21
gatccgagct caattaaccc tcactaaagg gagtcgactc gatccttaaa atattcatat    60
```

-continued

| | |
|---|---|
| ctcctggaca acctgtggcc atagtgcctg actgtaaacc caaagggttt gcctttgcca | 120 |
| gtgtagccca gcctggtgtc tgctgccct cgcggtgtct gtgcacctgc cacgatgctg | 180 |
| accagacacc cttaaccagg ttcacccatc gcctgggcct ggagcagtcc ccctgatgct | 240 |
| ctgattggtc cttggacctt ctgttctccc aaaatcccag gtcagaaaat acctggaagt | 300 |
| ctatttgtgt cccacctccc tctttgtggc cgcaagtgcc ccttcctcca cacagtcaca | 360 |
| agaccatgag atgccatctc ctcccctcct gggctgcaga ctttgggaag ctcccaggcc | 420 |
| acagaggtgt cagctcctgt ccaggccctt gggaccttcc ctcattcaac caccctaccc | 480 |
| aacccccac tgcctgccag ccaccactcc ctcccacatt tgcaggcggg ggccctgccc | 540 |
| tctcctgccg ctggttcccc tacccaggag gctctcccat cgctcttttg agagtctgcc | 600 |
| tcccacctct aactgggggc ttagttcaag ttgcccctt accctagtcc cagctgccca | 660 |
| agagcttgct gcctcctgtt cttggtgagg gactccagag acagatgtga gacctccctg | 720 |
| gacccctcca aggcattccc aggtcacttc catgagtagt gaagaaccgc ctctgagcag | 780 |
| gctgagcctc cctcagccta tggtgtcctc acgtggcttg gcccacagca ggtgctcacg | 840 |
| cctcctcctc agcagagcct accatcctcc tgccatgctc accagtcccc atgctgatag | 900 |
| ccatcaccag tccccatgct gatagccatc accagtcccc atgctgatag ccactttctg | 960 |
| gatgctctag gtctgtctgg atgacacagt gaccacagag aaggagctgg acactgtgga | 1020 |
| agtgctgaaa gcaattcaga aagccaagga ggtcaagtcc aaactgagca acccagagaa | 1080 |
| gaaggtgggt ttgtgtggca ggtgggaggg cagtggtgca gagccagccg ggataggagc | 1140 |
| cagttcgggg ggcttgggcc atgggactgc tcagggctgc cgagtcccag ctgcgcccct | 1200 |
| ccctggctgc atgacctcgg gcaagtcgcg gcctctctgt tctctgtggg gtggggacag | 1260 |
| tggtagttcc tgctctaagg atatgatgag accatcttta ccacccagtt ggtgggaacc | 1320 |
| gttgcgctcc ctcctcacac ccctggcctt ggggagctct gtgcttcctc ttctctcccg | 1380 |
| ggctgactca agcactcgtc ctcagggtgg tgaagactcc cggctctcag ctgcccctg | 1440 |
| catcagaccc agcagctccc ctcccactgt ggctcccgca tctgcctccc tgccccagcc | 1500 |
| catcctctct aaccaaggta atcgtgtatg tatcttgctt ctagtggagc cacacagccc | 1560 |
| tgcctgggcc ccctggctgg gctgggttg ggggagaggt gccagcacct gcttccaaca | 1620 |
| gggtcagaca cagggagggc agtgccttct gcaggctggt cctcgcgggg ggacacatgg | 1680 |
| caggggtgcc tggcctgatg ccagctgttg cttgcttggt gaggactccc aattgctctg | 1740 |
| atgcccacat ccagctcctc taggagaccg cagggtgtct gacaggccct gaggctgccc | 1800 |
| tctgaacagg ctcggggctg ttggctcatg ggacccattc cctcaccggc agcacaagca | 1860 |
| ggttggctcc tggttacagg aagccgggct tgtgacttta ctgtctggag cccgaatccc | 1920 |
| tgtgcaggga aaagcttgct tttatcactg cctcatctct gtggggtgac ccagccccag | 1980 |
| aacaccatgt ttgtggggcc aagatgggcc atctctgtcc ctgtggaccc atggaagacc | 2040 |
| aggcccattc gtctgcccac tatcttagcg ttttcaaagg gctttcacct ctgaacccag | 2100 |
| gcatcctcgg agatgagtga gtgaagcagg tctcatgagc gtgtctgctg gcccggcccc | 2160 |
| cacggaagag gggagggtgt gccgtcccga gtggagccga ggctcgggac acgcaggaaa | 2220 |
| ggacgccgcc tgcccgggct cctggagacg cagaacttgg tgtgaggtct tgggaaaaca | 2280 |
| gttcaacccg atgtttttaag agccagaaaa acattcccac cccttgacct ggtaacccca | 2340 |
| ctggtgggga ttttctctta gagggataag ataccgggaa ggggaggtga aatgctcacc | 2400 |
| actgccaaaa cacgggctgc aactgcaaca tcggaggatg agagggagag tcggctgtgg | 2460 |

-continued

```
tgcagaatgc tcagcagccc tcccagcagg gacaggaaga ctgggcagga agaggggaga    2520
agcattcaag ttaaggcaaa aggcccaacg cagagcagca cactgaggtc acacctgtga    2580
gatgtggaag agaattcctg agcgtggagc gatgggtta ggtgccagga tgattgccca    2640
ttttgcttct gtcagactct tgactaagga tttctggttg cattttatta cataaaagcc    2700
agggaggtta tatcacggtg agaaagcttc cctgacgccg cctcctgtag cgcagccaag    2760
cgagcctgtg gaggtaccat atgactgtag gcctctgggg acagggagct gcatctgctt    2820
ctcaaggcca gggacacagc catttctgcc agcatctgtt gatcagtgag tgagtgagtg    2880
ggcaggtaga gcaggagcca gtgaagagca ggccctggat gggtggggat gcaccatgtc    2940
cccaggctgc agctgcaggc agcccccac attgtcggag aagcctctgc accagctcag    3000 cccctcctc actccccttg tgccctgggg acactctgca gagggcact ctgcagtctg    3060 tccccgccat cgctggactt ctggacatgg cctccagatt tgcacctctt aaataaatct    3120
gcagtggatg tctttgtgtg cacctctctt tccttttggt gagaaacagc aaagatcgga    3180
cccctaagga ctctcctgat gtctccgctc tatccgctga gtgcccttc tgaccacttg    3240 tttgtacagg ccacggtcca ggacgggagc agatagactg tccctgtccc tgtccacatt    3300
tccttggtcc aaacagggct tgtgggaggt agtggcaaaa ggtgttggtc tttttctcac    3360
tgatttggag gcctccccgt gtgttttttc agccgcgtgt tcctgggtct tgcctggatg    3420
gacaggtttt tttagcgcgt gggagcagct ttgctgacca tgcctgttgc ttccagcctg    3480
attcccgaga agggagcgtg cttgcgaagg aactggcact cgggcctgcc tgaagggggc    3540
gctgtccaga cacacccagc ctcccgtcgt ggcaggcgct gtcggagcca tggatgattg    3600
tgaccaatag gggtggtcgc cagagttgat tgtccagcca ggcccagggg ctgagaggag    3660
gctgtgtgga gaggtggtta ggagccaggg ctcggtcagc tgagttcgca tgccagcttc    3720
ctagctgtgg gacctcaagc aacttgtagc ccctctgaag ctgttttctc aactgtgaag    3780
tggacgcacc ctacttcatt gattctaaga ggcacgcatt tccaccttgt gacttctctg    3840
aaactgaggt gcgtctttca gtcagtggcg tctcatagtc gctgtcagcc agctggtatt    3900
cgagatggag tcgtggaaaa cccgtggaca ccttccgcta ggaccaagat ggcgccacct    3960
gccgcatctt agatttgatg aaatgtggta aataacgaga ggcatgcatg agcgaatgct    4020
ggggaggcgc ttggcactac ccagagctcc acagaggtgg tcgatgaggg ctgccctttc    4080
ccacatcctt agtagggggt tcaacatgac ccagactgtg cccctgggga gcttggagcc    4140
atgcgggagg atgagccatg tgctggagga gaacagggta ggatggtgtg gggcttttgt    4200
agactgtcta gagcagagaa ggtctgcagt ggaggtggtg tctgaggtga atctcgaagg    4260
tgaataggag ttgaacgtta gcaggcagag ggtggattgc aggagagcag cggcctgggc    4320
aggtgcccag cgtggcccat cagggtgctt catgcatggc tgtgtgcttg ccatccttcc    4380
tgcctgccta ccccctgctg cttcgcttca tgggggcgtt tgagcttggg cccacctgcc    4440
tgcctcgctt gtgggcagag gacccaggct gtgtgagttg tcctgtcccg gggagcagct    4500
gagcttgtcc gggttcctcg acctgtgggg cttcagagga cttcgggtca tttcaatggg    4560
ctgtggcgat gctggctgtg gaggtagcct agggctcctg tagccttcag tgagactggc    4620
ggcccgatgc ccagtgttca ccctgctggc ggcagtcagg aacatgttca caaagctta    4680 cttcaagtgg tctagaggtg atctgaggtg gagtaacagg tccagatagg ctacgttcat    4740
aaaacagctt cagcggggtt taggaacact gtgcatttac gggacgcagt gggtcagagt    4800
```

```
gctgctgtcc gtgggaggtg gccccagggc aggtcagtgg gcacgtcctg tggtaagtgg     4860
gactgtggat gtgggctcag gctggactca gcagccctgc tggataccaa ggcctgcaag     4920
ggctggcccc ctggtgaatt gtcccgtgcc ctgtgtatct atgagtcctg cagagatgac     4980
aaatcagggg acgggtcat gtctagtcac cgtctgggaa aatgctccag gagtgaacac      5040
atttcaggct cttgatggat gtacctccaa actcttctct ggatgggtgg gccagcttgc     5100
atgcctgtgc cggcctctgc ccagcgaggt cagggccagg ccacacagtc agtctgactt     5160
tggcagaagt tgagaggcaa cacttgtctc ttgtttcagc ttgcctttct ttgtgtactt     5220
ctgagagcga gcattctttt catgttctat ccgctggccg ttcttctgcg gaatgtctgt     5280
tcacgtcctt tgcagtctgt taatgaggtt tccaaccttc cctcattttt gtaatctgta     5340
agaacttttt ccagactagc gatataaatc cttgtcaaat attgcaaaca cttttctcat     5400
ttcatctggt tttaatctat cctggttttt aaaaaatgtg tctgtggaag tttaatttt      5460 atgtagtcac atctcagttt ttttccattg catttattct cagaatgctt ctccctgccc     5520
tgagattaga taagcagtca tttgttcttt cttgagttat tttgagattt cagttttaac     5580
attttcttct ataatccatg tggctgggtt ttgggatctg gctaaccccc gccatgccag     5640
tagcctgagg ggcccagccc cacttgttga acagccgctc tccccgcccc acccaccctg     5700
cctgcctgcc caccgccct ggtctctcca ggaatcatgt tcgttcagga ggaggccctg      5760
gccagcagcc tctcgtccac tgacagtctg actcccgagc accagcccat tgcccaggga     5820
tgttctgatt ccttggagtc catccctgcg ggacaggtaa tgccctcttc ccgcttctgg     5880
ggaccataca tctgtgggtg gactcttctg cttgggggttg tgtgcagtag aagtggcct    5940 agctggagct gaggcagatg cttccagggt ttggcgtcct ctgctttgcg ccacggtctt     6000
tctcttggac ctgtctctgg ttgagtgtct tcctgacaaa cacagtggtt aagggtttat     6060
tttcagcctc cctccttccc ttccccaccc accttggttg atgggaacag gcagttctct     6120
gtcactgggc ccagggcacg agggggggcag gtggagaggg tggcccttga ccctgtgagc    6180
aggcttccct ggggaaggca tttcaaaaga ccctcgtgca ggggcttgtt tgggtttctt     6240
ctctgtttcc tggcaccct ggagccactc ggcgcctttc cgcatgtcac cctggtggtc     6300
tgggaaacag tctcactctg gcgcctcctc tgtggttgtt actgagagtt ctggggcccc     6360
ttcctttgtc ctgaggaaag acaggaggaa agcaagggtg cttgctgtgt gcttcgcaaa     6420
tgtgcttggt gcctgggcct ccctccagcc ccatctctgc agcagcacaa ggttatggcc     6480
ttgtgacact gggacagttt gcagagtcct tgtctgtcct cagtactcca cagtattctg     6540
ccatcaccct ttccagggtc acacagcaag agattcccaa gccctaggta ttccccagtg     6600
cacagagacc attgggaggg acttgccagg gctgtgtcca ctgctggcca gttagggtcg     6660
gaccaaattt gtagactgtc tacctggacc cttgcgtggc acaaggagca gtcagatgct     6720
ggatccctgg agagtggcga gaggctctgg ccttaggttg cgagtgggaa tcccagcct     6780 gctgtgtgct ggtgggataa ccaagtgggt ctctgccctt gggtcccaga gtgggcccca     6840
gggtcccaga gtgggctcca gggtacagcg tggggatggg gagcctcctc agggcggtga     6900
tggagggcag aatgcccagc tcagggtctg gcaaccagta aatggctggg gctggctgca     6960
gtaggtgggg actgactgtg tttctttctc catcaggcag cttccgatga tttaagggac     7020
gtgccaggag ctgttggtgg tgcaaggtaa ggaagaggtt ggaaagggac ctgggcctgg     7080
ccacacagcc ttatgcacac acactgctgt gggccagggg tggccagtca ggttttttta     7140
aaaatccgtt cacagaaggc ctatagaact atttcttcct ctaaagagac acagatgaga     7200
```

-continued

```
tggactttc  aatctgtttc  caaattctaa  tacctaaact  ctgctcagca  catgttgccc    7260
tacaccaggg  gttggcaaat  caaggcctgt  gtgtggccca  cagcctggga  gctaagaatg    7320
acagttacat  tcttttttct  ttttttgaga  ctgagtctcg  ctctgtcgcc  caggctggag    7380
tgcagtggcg  tgttcttggc  tcactgcaac  ccccgcctcc  cagattaatg  caattttcct    7440
gtctcagcct  cagccttctg  agtagcccgg  accacaggcg  cacgccacca  cgcccaacta    7500
attttttata  ttttagtag   agacagagat  tcaccatgtg  gcctagctgg  tctcgaactc    7560
ctgaactcca  gtgatccacc  aacctcggct  tcctaaagta  ctggaattac  aggcatgagc    7620
caccgcgcct  ggctagaata  acagttactt  ttttttttctt  tgagactgag  tcttgctttg    7680
tcacccaggc  tggagtgcag  tggcacgatc  tcagctcgct  gcaacctccg  cctcccgggt    7740
tcaagcgatt  cttctgcctc  agccacccaa  ggtgcccgcc  accacacctg  gctaattttt    7800
ctgtttttag  tagggacagg  atttcgccat  gttggacagt  tacattctta  aagggctgct    7860
gaagatcgta  tggacatggt  agcccataaa  tcccaaaatg  tgtactctga  ccctttacag    7920
aagcttacta  actcccactc  tacatgtgag  ggctgcggtg  gccaagaaga  gctgaatt t    7980 aagtgtgaag  gtcctaagac  ctgccccagc  ccacttccct  gccccggagg  ccaccagggg    8040
tgacaagtag  attcatgccc  tggagtgttc  cttctctccg  gggcttatgg  cagcaactga    8100
atgacttaga  agtccatggg  agtgcttct   gttgtgggaa  ctcgtgtggt  ctgggcatag    8160
ctgtgccagg  cacctatggt  ccaagcccct  agaagcatag  actctgacca  aactggcgac    8220
ccagccttcc  agcaggcagc  actggctccc  accagggccc  tcatcctggg  aactgacttg    8280
gccatgtggg  aggcttggga  gacccatggg  ttggtttctc  agggtcaggg  tgtagcagtg    8340
ggctccagat  gtggcaggtg  ggaggtggga  ggggccctc   ccagcatgcc  actgacctgg    8400
cctctccctg  cacagcccag  aacatgccga  gccggaggtc  caggtggtgc  cggggtctgg    8460
ccagatcatc  ttcctgccct  tcacctgcat  tggctacacg  gccaccaatc  aggacttcat    8520
ccagcgcctg  agcacactga  tccggcaggc  catcgagcgg  cagctgcctg  cctggatcga    8580
ggctgccaac  cagcgggagg  agggccaggg  tgaacagggc  gaggaggagg  atgaggagga    8640
ggaagaagag  gaggacgtgg  ctgagaaccg  ctactttgaa  atggggcccc  cagacgtgga    8700
ggaggaggag  ggaggaggcc  agggggagga  agaggaggag  gaagaggagg  atgaagaggc    8760
cgaggaggag  cgcctggctc  tggaatgggc  cctgggcgcg  gacgaggact  tcctgctgga    8820
gcacatccgc  atcctcaagg  tgctgtggtg  cttcctgatc  catgtgcagg  gcagtatccg    8880
ccagttcgcc  gcctgccttg  tgctcaccga  cttcggcatc  gcagtcttcg  agatcccgca    8940
ccaggagtct  cggggcagca  gccagcacat  cctctcctcc  ctgcgctttg  tcttttgctt    9000
cccgcatggc  gacctcaccg  agtttggctt  cctcatgccg  gagctgtgtc  tggtgctcaa    9060
ggtacggcac  agtgagaaca  cgctcttcat  tatctcggac  gccgccaacc  tgcacgagtt    9120
ccacgcggac  ctgcgctcat  gctttgcacc  ccagcacatg  gccatgctgt  gtagcccat    9180 cctctacggc  agccacacca  gcctgcagga  gttcctgcgc  cagctgctca  ccttctacaa    9240
ggtggctggc  ggctgccagg  agcgcagcca  gggctgcttc  cccgtctacc  tggtctacag    9300
tgacaagcgc  atggtgcaga  cggccgccgg  ggactactca  gcaacatcg   agtgggccag    9360 ctgcacactc  tgttcagccg  tgcggcgctc  ctgctgcgcg  ccctctgagg  ccgtcaagtc    9420
cgccgccatc  ccctactggc  tgttgctcac  gccccagcac  ctcaacgtca  tcaaggccga    9480
cttcaacccc  atgcccaacc  gtggcaccca  caactgtcgc  aaccgcaaca  gcttcaagct    9540
```

-continued

```
cagccgtgtg ccgctctcca ccgtgctgct ggaccccaca cgcagctgta cccagcctcg      9600
gggcgccttt gctgatggcc acgtgctaga gctgctcgtg gggtaccgct ttgtcactgc      9660
catcttcgtg ctgccccacg agaagttcca cttcctgcgc gtctacaacc agctgcgggc      9720
ctcgctgcag gacctgaaga ctgtggtcat cgccaagacc cccgggacgg gaggcagccc      9780
ccagggctcc tttgcggatg ccagcctgc cgagcgcagg gccaggtgag atcaagcaca       9840
gctctcaggg gccccggggg cacgggtctg gcatgtgtgt gatctcagca tctgcggcta     9900
gtgtgggctg ggagttgctg cgagagctgg gccccctccc cctgcccct cgccccccc       9960 gggcctccct ctacatcacc accccaggtt tggtgccagg ctgctcctta tctcagtgct    10020
gtagaagaag cccaggaaag ctgtcctctc acaaaatggg ttggcccagc ctcttgccac    10080
ccatgaaggc aggccaagg gggctgcccc acctttgcct gcccagtggg agagcaacag     10140
gctgcagcac accgaggcca ggagagctgt caccctggct gctgtgctcc tctgggccca    10200
agcatggcct ctgggcacta cctcctccag ggtcacagtc ccacgatgg ctctgtgggc     10260 caggatctgc cttaggcttc acccacctca acatcttgct gtgttgttca ggctggtctc    10320
aaactttggg ctcaaacaat cctccgcctc agcctcccaa agtgctggga ttacagacat    10380
gagccaccgt gcccggccgt gctgttctgt tctccaatag agaagctggt ggaagtcccc    10440
agtaacccag aggtgatgtg tgatgcacac agtctcctca ctctgaagct gcacatgcga    10500
tgtgaatctt catttggggt ccgctgttaa tatggtgttt ttcgggggat acagcaatga    10560
ccagcgtccc caggaggtcc cagcagaggc tctggccccg gccccagtgg aagtcccagc    10620
tccagcccct gcagcagcct cagcctcagg cccagcgaag actccggccc cagcagaggc    10680
ctcaacttca gctttggtcc cagaggagac gccagtggaa gctccagccc cacccccagc    10740
cgaggcccct gcccagtacc cgagtgagca cctcatccag gccacctcgg aggagaatca    10800
gatcccctcg cacttgcctg cctgcccgtc gctccggcac gtcgccagcc tgcgggggcag   10860 cgccatcatc gagctcttcc acagcagcat tgctgaggta gcggcccggg tgtgggtgcc    10920
agctatggca cggccagtcc tgagggcgag gccaagcttg gcttcaggtc agcctcaggt    10980
ccctggactt ccctgatgtc ggagtcctca gctgagctgc tcacagcttt gaggacctgg    11040
gcagtgaggt cctgagttgc cctccctggc catttgtgct gtgtcaccac ctcctgtgcc    11100
acttccagcc ccaggtagac ctcccaccaa cagccatctc ccaccctct cttcctctct     11160 gccttgaagc atacggattc attggtgagc aagaggggc ttcccatgtc tccttgtgga     11220
agctgtgggc atgtccctgg tatgtgcagg ttgctagggt ggtggagctg acaggaggcc    11280
ccccgtcttc aggttgaaaa cgaggagctg aggcacctca tgtggtcctc ggtggtgttc    11340
taccagaccc cagggctgga ggtgactgcc tgcgtgctgc tctccaccaa ggctgtgtac    11400
tttgtgctcc acgacggcct ccgccgctac ttctcagagc cactgcaggg taggcacagg    11460
gcctgctggg gctcaggagc ttggagtgtg tggttgggc aggcctgggg ggtcattctc     11520
tggagccagc tgtgtggctt caggcagcag tcagcgactt ggctgcagtg ggctgagagt    11580
tccttgtctg aggaagggag ctgtcatgag ggagggtcc atggccagat gtgaacgcag     11640
aatgcactga gccagggcct ggtgactgct tgggaacagc ctgtgatgag aagggggttag   11700 gcagcctttg cccctgggc tgcacaggaa gccctagcca gcgacctggt gactcccctg     11760
agctggaaga ggctcagact ccagagggca ttgcctatgg ggctttgcac gggtggaagc    11820
caggccagcc aagaggacct gttcctgctg gatgtgctgc acacctagga accttgtgct    11880
tgcctgccac cgcctcccctc tgtcccttt tccatcacac agatttctgg catcagaaaa    11940
```

-continued

```
acaccgacta caacaacagc cctttccaca tctcccagtg cttcgtgcta aagcttagtg    12000
acctgcagtc agtcaatgtg gggcttttcg accagcattt ccggctgacg cgtgggtgac    12060
cctctgtgct ttgtcctatt tcgggtgaag gccagcatca ccagtgggct tccaccttcc    12120
gtacgtgggt gggttatcat agacagttat ctctgtgctc aagagccact tcttacccgg    12180
ggtgggagga agcagcttca ggaactgctg agagagcaga actcacgctc cagggctcag    12240
agcaggaggt agggtgtgcg gcaagcgctg gcccggacag aagcagagtg ggccctggtc    12300
tcgggcagga tgtttctgac tcacatttcc tgaggagaga aagctaagct ctttgcctaa    12360
tgtctctgtc tccccttcca gaaaaatgcc tcagctcttc cggcctgaag gaatggcctc    12420
ctcccgggcc ccatgattct ttcctgtgtg ggccctcctg gccctggcct ctgggctgag    12480
gcttgctagg gactcggggt ggctctaagg ggcagggata gggctgggga gcgccggcct    12540
gtggccctga ccagcccctt ctcgtgcagg ttccacccCg atgcaggtgg tcacgtgctt    12600
gacgcgggac agctacctga cgcactgctt cctccagcac ctcatggtcg tgctgtcctc    12660
tctggaacgc acgccctcgc cggagcctgt tgacaaggac ttctactccg agtttgggaa    12720
caagaccaca ggtaccccctg tctagctcag gctgcagaca ggctgcctgg acagacgtca    12780
tgggccccag ggtggctctc tgtgcCccag aaccctctct gcctctatgt ctctcttttc    12840
tcacttagct ggccagggtt ttatgtgggg cttttcgatg gcagagtctc cactccagca    12900
gtccctcaac catctggcag acacatctcc agtgcctgct ttgggctcct ggcctgtggg    12960
ccccacactt ggagcatcct ctcctgcctg tctcatgccg gggtctctcg gttggcttgg    13020
ggcccttggt gctcccagcc ccaccagggg ccggttccag gctatagccc aggtggcatc    13080
tctctgcagg gaagatggag aactacgagc tgatccactc tagtcgcgtc aagtttacct    13140
accccagtga ggaggagatt ggggacctga cgttcactgt ggcccaaaag atggctgagc    13200
cagagaaggc cccagccctc agcatcctgc tgtacgtgca ggccttccag gtgggcatgc    13260
cacccccctgg gtgctgcagg ggccccctgc gccccaagac actcctgctc accagctccg    13320
agatcttcct cctggatgag gactgtgtcc actacccact gcccgagttt gccaaagagc    13380
cgccgcagag agacaggtac cggctggacg atggccgccg cgtccgggac ctggaccgag    13440
tgctcatggg ctaccagacc tacccgcagg ccctcaccct cgtcttcgat gacgtgcaag    13500
gtcatgacct catgggcagt gtcaccctgg accactttgg ggaggtgcca ggtggcccgg    13560
ctagagccag ccagggccgt gaagtccagt ggcaggtgtt tgtccccagt gctgagagca    13620
gagagaagct catctcgctg ttggctcgcc agtgggaggc cctgtgtggc cgtgagctgc    13680
ctgtcgagct caccggctag cccaggccac agccagcctg tcgtgtccag cctgacgcct    13740
actggggcag ggcagcaggc ttttgtgttc tctaaaaatg ttttatcctc cctttggtac    13800
cttaatttga ctgtcctcgc agagaatgtg aacatgtgtg tgtgttgtgt taattctttc    13860
tcatgttggg agtgagaatg ccgggcccct cagggctgtc ggtgtgctgt cagcctccca    13920
caggtggtac agccgtgcac accagtgtcg tgtctgctgt tgtgggaccg ttgttaacac    13980
gtgacactgt gggtctgact ttctcttcta cacgtccttt cctgaagtgt cgagtccagt    14040
cctttgttgc tgttgctgtt gctgttgctg ttgctgttgg catcttgctg ctaatcctga    14100
ggctggtagc agaatgcaca ttggaagctc ccaccccata ttgttcttca aagtggaggt    14160
ctccctgat ccagacaagt gggagagccc gtggggcag gggacctgga gctgccagca    14220
ccaagcgtga ttcctgctgc ctgtattctc tattccaata aagcagagtt tgacaccgtc    14280
```

-continued

```
tgcatcttct aaaccaaggg tcactgggat cgagtcgacg gccctatagt gagtcgtatt    14340
agagctcgcg gccgcgagct ctagatgcat gctcgagcgg ccgccagtgt gatggatatc    14400
tgcagaattc cagcacactg gcggccgtta ctagtggatc cgagctccac agaggtggtc    14460
gatgagggct gcccttccc acatccttag taggggttc aagatgaccc agactgtgcc      14520
cctggggagc ttggagccat gcgggaggat gagccatgtg ctggaggaga acagggtagg    14580
atggtgtggg gcttttgtag actgtctaga agcaaagaag gtctgcagtg gaggtggtgt    14640
ctgaggtgaa tctcgaaggt gaataggagt tgaacgttag caggcagagg gtggattgca    14700
ggagagcagc ggcctgggca ggtgcccagc gtggcccatc agggtgcttc atgcatggct    14760
gtgtgcttgc catccttcct gcctgcctac cccctgctgc ttcgcttcat ggggcgttt     14820
gagcttgggc ccacctgcct gcctcgcttg tgggcagagg acccaagctg tgtgagttgt    14880
cctgtcccgg ggagcagctg aactggtccg ggtctcgaa ctgtgggct caaaaggact      14940
ccggggtcat ttcactgggg ctgtgccgat tcctgggggc tgttnggaan gtaaaggcct    15000
aaagggctc cctggttang gccctcaant ttaanaacct ggggccgggg cccggaattg     15060
cccccaantt tgtttcaacn ccccttggcc ttnggcnggg gcaaatttcc anggggaacc    15120
aatggntttc ccccaaaaan ggggccnttt taacccnttt ccaaantttg ggncctaaaa    15180
aagggtggan ttcctgaang gg                                             15202
```

<210> SEQ ID NO 22
<211> LENGTH: 1070
<212> TYPE: PRT
<213> ORGANISM: Homo sapiens

<400> SEQUENCE: 22

```
Val Cys Leu Asp Asp Thr Val Thr Thr Glu Lys Glu Leu Asp Thr Val
  1               5                  10                  15

Glu Val Leu Lys Ala Ile Gln Lys Ala Lys Glu Val Lys Ser Lys Leu
             20                  25                  30

Ser Asn Pro Glu Lys Lys Gly Gly Glu Asp Ser Arg Leu Ser Ala Ala
         35                  40                  45

Pro Cys Ile Arg Pro Ser Ser Pro Pro Thr Val Ala Pro Ala Ser
     50                  55                  60

Ala Ser Leu Pro Gln Pro Ile Leu Ser Asn Gln Gly Ile Met Phe Val
 65                  70                  75                  80

Gln Glu Glu Ala Leu Ala Ser Ser Leu Ser Ser Thr Asp Ser Leu Thr
                 85                  90                  95

Pro Glu His Gln Pro Ile Ala Gln Gly Cys Ser Asp Ser Leu Glu Ser
            100                 105                 110

Ile Pro Ala Gly Gln Ala Ala Ser Asp Asp Leu Arg Asp Val Pro Gly
        115                 120                 125

Ala Val Gly Gly Ala Ser Pro Glu His Ala Glu Pro Glu Val Gln Val
    130                 135                 140

Val Pro Gly Ser Gly Gln Ile Ile Phe Leu Pro Phe Thr Cys Ile Gly
145                 150                 155                 160

Tyr Thr Ala Thr Asn Gln Asp Phe Ile Gln Arg Leu Ser Thr Leu Ile
                165                 170                 175

Arg Gln Ala Ile Glu Arg Gln Leu Pro Ala Trp Ile Glu Ala Ala Asn
            180                 185                 190

Gln Arg Glu Glu Gly Gln Gly Glu Gln Gly Glu Glu Asp Glu Glu
        195                 200                 205
```

```
Glu Glu Glu Glu Glu Asp Val Ala Glu Asn Arg Tyr Phe Glu Met Gly
    210                 215                 220
Pro Pro Asp Val Glu Glu Glu Gly Gly Gln Gly Glu Glu Glu
225                 230                 235                 240
Glu Glu Glu Glu Glu Asp Glu Glu Ala Glu Glu Arg Leu Ala Leu
                245                 250                 255
Glu Trp Ala Leu Gly Ala Asp Glu Asp Phe Leu Leu Glu His Ile Arg
            260                 265                 270
Ile Leu Lys Val Leu Trp Cys Phe Leu Ile His Val Gln Gly Ser Ile
            275                 280                 285
Arg Gln Phe Ala Ala Cys Leu Val Leu Thr Asp Phe Gly Ile Ala Val
    290                 295                 300
Phe Glu Ile Pro His Gln Glu Ser Arg Gly Ser Ser Gln His Ile Leu
305                 310                 315                 320
Ser Ser Leu Arg Phe Val Phe Cys Phe Pro His Gly Asp Leu Thr Glu
                325                 330                 335
Phe Gly Phe Leu Met Pro Glu Leu Cys Leu Val Leu Lys Val Arg His
            340                 345                 350
Ser Glu Asn Thr Leu Phe Ile Ile Ser Asp Ala Ala Asn Leu His Glu
            355                 360                 365
Phe His Ala Asp Leu Arg Ser Cys Phe Ala Pro Gln His Met Ala Met
    370                 375                 380
Leu Cys Ser Pro Ile Leu Tyr Gly Ser His Thr Ser Leu Gln Glu Phe
385                 390                 395                 400
Leu Arg Gln Leu Leu Thr Phe Tyr Lys Val Ala Gly Cys Gln Glu
                405                 410                 415
Arg Ser Gln Gly Cys Phe Pro Val Tyr Leu Val Tyr Ser Asp Lys Arg
            420                 425                 430
Met Val Gln Thr Ala Ala Gly Asp Tyr Ser Gly Asn Ile Glu Trp Ala
            435                 440                 445
Ser Cys Thr Leu Cys Ser Ala Val Arg Arg Ser Cys Cys Ala Pro Ser
    450                 455                 460
Glu Ala Val Lys Ser Ala Ala Ile Pro Tyr Trp Leu Leu Leu Thr Pro
465                 470                 475                 480
Gln His Leu Asn Val Ile Lys Ala Asp Phe Asn Pro Met Pro Asn Arg
                485                 490                 495
Gly Thr His Asn Cys Arg Asn Arg Asn Ser Phe Lys Leu Ser Arg Val
            500                 505                 510
Pro Leu Ser Thr Val Leu Leu Asp Pro Thr Arg Ser Cys Thr Gln Pro
    515                 520                 525
Arg Gly Ala Phe Ala Asp Gly His Val Leu Glu Leu Leu Val Gly Tyr
    530                 535                 540
Arg Phe Val Thr Ala Ile Phe Val Leu Pro His Glu Lys Phe His Phe
545                 550                 555                 560
Leu Arg Val Tyr Asn Gln Leu Arg Ala Ser Leu Gln Asp Leu Lys Thr
                565                 570                 575
Val Val Ile Ala Lys Thr Pro Gly Thr Gly Gly Ser Pro Gln Gly Ser
            580                 585                 590
Phe Ala Asp Gly Gln Pro Ala Glu Arg Arg Ala Ser Asn Asp Gln Arg
    595                 600                 605
Pro Gln Glu Val Pro Ala Glu Ala Leu Ala Pro Ala Pro Val Glu Val
    610                 615                 620
Pro Ala Pro Ala Pro Ala Ala Ala Ser Ala Ser Gly Pro Ala Lys Thr
```

```
            625                 630                 635                 640
Pro Ala Pro Ala Glu Ala Ser Thr Ser Ala Leu Val Pro Glu Glu Thr
                645                 650                 655
Pro Val Glu Ala Pro Ala Pro Pro Ala Glu Ala Pro Ala Gln Tyr
                660                 665                 670
Pro Ser Glu His Leu Ile Gln Ala Thr Ser Glu Glu Asn Gln Ile Pro
                675                 680                 685
Ser His Leu Pro Ala Cys Pro Ser Leu Arg His Val Ala Ser Leu Arg
                690                 695                 700
Gly Ser Ala Ile Ile Glu Leu Phe His Ser Ser Ile Ala Glu Val Glu
705                 710                 715                 720
Asn Glu Glu Leu Arg His Leu Met Trp Ser Ser Val Val Phe Tyr Gln
                725                 730                 735
Thr Pro Gly Leu Glu Val Thr Ala Cys Val Leu Leu Ser Thr Lys Ala
                740                 745                 750
Val Tyr Phe Val Leu His Asp Gly Leu Arg Arg Tyr Phe Ser Glu Pro
                755                 760                 765
Leu Gln Asp Phe Trp His Gln Lys Asn Thr Asp Tyr Asn Asn Ser Pro
                770                 775                 780
Phe His Ile Ser Gln Cys Phe Val Leu Lys Leu Ser Asp Leu Gln Ser
785                 790                 795                 800
Val Asn Val Gly Leu Phe Asp Gln His Phe Arg Leu Thr Gly Ser Thr
                805                 810                 815
Pro Met Gln Val Val Thr Cys Leu Thr Arg Asp Ser Tyr Leu Thr His
                820                 825                 830
Cys Phe Leu Gln His Leu Met Val Val Leu Ser Ser Leu Glu Arg Thr
                835                 840                 845
Pro Ser Pro Glu Pro Val Asp Lys Asp Phe Tyr Ser Glu Phe Gly Asn
                850                 855                 860
Lys Thr Thr Gly Lys Met Glu Asn Tyr Glu Leu Ile His Ser Ser Arg
865                 870                 875                 880
Val Lys Phe Thr Tyr Pro Ser Glu Glu Ile Gly Asp Leu Thr Phe
                885                 890                 895
Thr Val Ala Gln Lys Met Ala Glu Pro Glu Lys Ala Pro Ala Leu Ser
                900                 905                 910
Ile Leu Leu Tyr Val Gln Ala Phe Gln Val Gly Met Pro Pro Gly
                915                 920                 925
Cys Cys Arg Gly Pro Leu Arg Pro Lys Thr Leu Leu Leu Thr Ser Ser
                930                 935                 940
Glu Ile Phe Leu Leu Asp Glu Asp Cys Val His Tyr Pro Leu Pro Glu
945                 950                 955                 960
Phe Ala Lys Glu Pro Pro Gln Arg Asp Arg Tyr Arg Leu Asp Asp Gly
                965                 970                 975
Arg Arg Val Arg Asp Leu Asp Arg Val Leu Met Gly Tyr Gln Thr Tyr
                980                 985                 990
Pro Gln Ala Leu Thr Leu Val Phe Asp Val Gln Gly His Asp Leu
                995                 1000                1005
Met Gly Ser Val Thr Leu Asp His Phe Gly Glu Val Pro Gly Gly Pro
                1010                1015                1020
Ala Arg Ala Ser Gln Gly Arg Glu Val Gln Trp Gln Val Phe Val Pro
1025                1030                1035                1040
```

-continued

```
Ser Ala Glu Ser Arg Glu Lys Leu Ile Ser Leu Leu Ala Arg Gln Trp
            1045                1050                1055

Glu Ala Leu Cys Gly Arg Glu Leu Pro Val Glu Leu Thr Gly
            1060                1065                1070
```

IMIDAZOLINE RECEPTIVE POLYPEPTIDES

REFERENCE TO RELATED APPLICATION

This application is a division of application Ser. No. 08/922,635, filed Sep. 3, 1997, U.S. Pat. No. 6,033,871, which is a continuation-in-part of application Ser. No. 08/650,766, filed May 20, 1996, U.S. Pat. No. which is related to provisional application Ser. No. 60/012,600, filed Mar. 1, 1996, abandoned.

BACKGROUND OF THE INVENTION

1. Field of the Invention

The present invention is directed to DNA molecules encoding imidazoline receptive polypeptides, preferably encoding human imidazoline receptive polypeptides, that can be used as an imidazoline receptor (abbreviated IR). In addition, transcript(s) and protein sequences are predicted from the DNA clones. The invention is also directed to a genomic DNA clone designated as JEP-1A. The cDNA clones according to the invention comprise cDNA homologous to portion(s) of this genomic clone; including 5A-1 cDNA, cloned by the inventors that established the open-reading frame for translation of mRNA from the gene, and established the immunoreactive properties of its polypeptide sequence in an expression systems. Also, the invention relates to cDNA clone EST04033, which is another clone identified to contain cDNA sequences from the JEP-1A gene, and of which the 5A-1 is a part, that encodes an active fragment of the IR polypeptide in transfection assays, and the protein sequences thereof. The invention also relates to methods for producing such genomic and cDNA clones, methods for expressing the IR protein and fragments, and uses thereof.

2. Description of Related Art

It is believed that brainstem imidazoline receptors possess binding site(s) for therapeutically relevant imidazoline compounds, such as clonidine and idazoxan. These drugs represent the first generation of ligands discovered for the binding site(s) of imidazoline receptors. However, clonidine and idazoxan were developed based on their high affinity for $\alpha_2$-adrenergic receptors. Second generation ligands, such as moxonidine, possess somewhat improved selectivity for IR over $\alpha_2$-adrenergic receptors, but more selective compounds for IR are needed.

An imidazoline receptor clone is of particular interest because of its potential utility in identifying novel pharmaceutical agents having greater potency and/or more selectivity than currently available ligands have for imidazoline receptors. Recent technological advances permit pharmaceutical companies to use combinatorial chemistry techniques to rapidly screen a cloned receptor for ligands (drugs) binding thereto. Thus, a cloned imidazoline receptor would be of significant value to a drug discovery program.

Until now, the molecular nature of imidazoline receptors remains unknown. For instance, no amino acid sequence data for a novel IR, e.g., by N-terminal sequencing, has been reported. Three different techniques have been described in the literature by three different laboratories to visualize imidazoline-selective binding proteins (imidazoline receptor candidates) using gel electrophoresis. Some important consistencies have emerged from these results despite the diversity of the techniques employed. On the other hand, multiple protein bands have been identified, which suggests heterogeneity amongst imidazoline receptors. These reports are discussed below.

Some of the abbreviations used hereinbelow, have the following meanings:

| | |
|---|---|
| $\alpha_2$AR | Alpha-2 adrenoceptor |
| BAC | Bovine adrenal chromaffin |
| ECL | Enhanced chemiluminescence (protein detection procedure) |
| EST | Expressed Sequence Tag (a one-pass cDNA documentation without identification) |
| I-site | Any imidazoline-receptive binding site (e.g., encoded on IR) |
| $IR_1$ | Imidazoline receptor subtype$_1$ |
| IR-Ab | Imidazoline receptor antibody |
| $I_2$Site | Imidazoline binding subtype$_2$ |
| kDa | Kilodaltons (molecular size) |
| MAO | monoamine oxidase |
| MW | molecular weight |
| NRL | European abbreviation for RVLM (see below) |
| PC-12 | Phaeochromocytoma-12 cells |
| $^{125}$PIC | [$^{125}$I]p-iodoclonidine |
| PKC | Protein Kinase C |
| RVLM | Rostral Ventrolateral Medulla in brainstem |
| SDS | sodium dodecyl sulfate gel electrophoresis |

Reis et al. [Wang et al., *Mol. Pharm.*, 42: 792–801 (1992); Wang et al., Mol. Pharm., 43: 509–515 (1993)] were the first to characterize an imidazoline-selective binding protein and to demonstrate it as having MW=70 kDa. This was accomplished using bovine cells (BAC), which lack an $\alpha_2$AR [Powis & Baker, *Mol. Pharm.*, 29:134–141 (1986)]. The 70 kDa imidazoline-selective protein in those studies had high affinities for both idazoxan and p-aminoclonidine affinity chromatography columns and was eluted by another imidazoline compound (phentolamine). Unfortunately, those investigators failed to isolate sufficient 70 kDa protein to determine its other biochemical properties. To date, no one has reported the complete purification of an imidazoline receptor protein. Likewise, no amino acid sequences have been reported for IR.

Their 70 kDa protein was used by Reis and co-workers to raise "I-site binding antiserum", designated herein as Reis antiserum. The term "I-site" refers to the imidazoline binding site, presumably defined within the imidazoline receptor protein. Reis antiserum was prepared by injecting the purified protein into rabbits [Wang et al, 1992]. The first immunization was done subcutaneously with the protein antigen (10 µg) emulsified in an equal volume of complete Freund's adjuvant, and the next three booster shots were given at 15-day intervals with incomplete Freund's adjuvant. The polyclonal antiserum has been mostly characterized by immunoblotting, but radioimmunoassays (RIA) and/or conjugated assay procedures, i.e., ELISA assays, are also conceivable [see "Radioimmunoassay of Gut Regulatory Peptides: Methods in Laboratory Medicine," Vol. 2, chapters 1 and 2, Praeger Scientific Press, 1982].

The present inventors and others [Escriba et al., *Neurosci. Lett.* 178: 81–84 (1994)] have characterized the Reis antiserum in several respects. For instance, the present inventors have discovered that human platelet immunoreactivity with Reis antiserum is mainly confined to a single protein band of MW≈33 kDa, although a trace band at ≈85 kDa was also observed. The ≈33 and ≈85 kDa bands were enriched in plasma membrane fractions as expected for an imidazoline receptor. Furthermore, the intensity of the ≈33 kDa band was found to be positively correlated with non-adrenergic $^{125}$PIC Bmax values at platelet $IR_1$ sites in samples from the same subjects, with an almost one-to-one slope factor. In addition, the nonadrenergic $^{125}$PIC binding sites on platelets were discovered by the present inventors to have the same rank order of affinities as $IR_1$ binding sites in brainstem [Piletz and Sletten, J. Pharm. & Exper. Therap., 267: 1493–1502 (1993)]. The platelet≈33 kDa band may also be a product of a larger protein, since in human megakaryoblastoma cells, which are capable of forming platelets in tissue cultures, an ≈85 kDa immunoreactive band was found to predominate.

Immunoreactivity with Reis antiserum does not appear to be directed against human $\alpha_2AR$ and/or MAO A/B. This is a significant point because $\alpha_2AR$ and MAO A/B have previously been cloned and also bind to imidazolines. The present inventors have obtained selective antibodies and recombinant preparations for $\alpha_2AR$ and MAO A/B, and these proteins do not correspond to the ≈33, 70, or 85 kDa putative $IR_1$ bands. Thus, there is substantial evidence that, at least in human platelets, the Reis antiserum is $IR_1$ selective.

Another antiserum was raised by Drs. Dontenwill and Bousquet in France [Greney et al., Europ. J. Pharmacol., 265: R1–R2 (1994); Greney et al., Neurochem. Int., 25: 183–191 (199.4); Bennai et al., Annals NY Acad. Sci., 763:140–148 (1995)] against polyclonal antibodies for idazoxan (designated Dontenwill antiserum). This anti-idiotypic antiserum inhibits $^3$H-clonidine but not $^3$H-rauwolscine ($\alpha_2$-selective) binding sites in the brainstem, suggesting it also interacts with $IR_1$ [Bennai et al., 1995]. As shown in FIG. 1, human RVLM (same as NRL) membrane fractions displayed bands of ≈41 and 44 kDa, as detected by the present inventors using this anti-idiotypic antiserum.

The present inventors have found that the bands of MW≈41 and 44 kDa detected by Dontenwill antiserum may be derived from an ≈85 kDa precursor protein, similar to that occurring in platelet precursor cells. An 85 kDa immunoreactive protein is obtained in fresh rat brain membranes only when a cocktail of 11 protease inhibitors is used. Also, as shown in FIG. 1, it is found that Reis antiserum detects the ≈41 and 44 kDa bands in human brain when fewer protease inhibitors are used. Additionally, the Dontenwill antiserum weakly detects a platelet ≈33 kDa band. Thus, the present inventors have hypothesized that the ≈41 and 44 kDa immunoreactive proteins may be alternative breakdown products of an ≈85 kDa protein, as opposed to the platelet≈33 kDa breakdown product.

In summary, the main conclusion from the above results is that, despite vastly different origins, the Reis and Dontenwill antisera both detect identical bands in human platelets, RVLM, and hippocampus.

Using yet another technique, a photoaffinity imidazoline ligand, $^{125}$AZIPI, has also been developed to preferentially label $I_2$-imidazoline binding sites [Lanier et al., J. Biol. Chem., 268: 16047–16051 (1993)]. The $^{125}$AZIPI photoaffinity ligand was used to visualize ≈55 kDa and ≈61 kDa binding proteins from rat liver and brain. It is believed that the ≈61 kDa protein is probably MAO, in agreement with other findings [Tesson et al., J. Biol. Chem., 270: 9856–9861 (1995)] showing that MAO proteins bind certain imidazoline compounds. The different molecular weights between these bands and those detected immunologically by the present inventors is one of many pieces of evidence that distinguishes $IR_1$ from $I_2$ sites.

To the inventors' knowledge and as described herein, we are first to clone the gene, cDNAs and fragments thereof encoding a protein with the immunological and ligand binding properties expected of an IR. on this basis, we are first to identify the nucleotide sequences of DNA molecules encoding an imidazoline receptor and active fragments thereof, and the first to determine the amino acid sequence of an imidazoline receptor and active fragments thereof. The polypeptides described herein are clearly distinct from $\alpha_2AR$ or MAO A/B proteins.

SUMMARY OF THE INVENTION

The present invention involves various cDNA clones (ie., 5A-1 and EST04033) and a genomic clone (JEP-1A) which are directed to an isolated polypeptide(s) that is receptive to (bind to) imidazoline compound(s), and can be used to identify other compounds of interest. Currently available imidazoline compounds in this context are p-iodoclonidine and moxonidine. Initially, the inventors detected a polypeptide expressed by their cDNA clone (5A-1 isolated from a human hippocampus cDNA library) that immunoreacted with Reis antiserum and/or Dontenwill antiserum. The DNA sequence of the 5A-1 clone is encapsulated within a portion of the other clones (EST04033 and JEP-1A genomic clone).

In one aspect of the invention, a polypeptide includes a 651 amino acid sequence as shown in SEQ ID No. 5. This polypeptide is predicted from non-plasmid cDNA in EST04033; a clone which the inventors showed possesses sequences inclusive of 5A-1. Furthermore, transfection of EST04033 into COS cells yielded imidazoline receptivity by radioligand binding assays (described in detail later). Other imidazoline receptive proteins homologous to this polypeptide are also contemplated. Such polypeptide(s) generally have a molecular weight of about 50 to 80 kDa. More particularly, one can have a molecular weight of about 70 kDa.

In another aspect of this invention, a polypeptide includes a 390 amino acid sequence as shown in SEQ ID No. 6. This represents the polypeptide predicted from the non-plasmid DNA of the original 5A-1 clone. Such a polypeptide generally has a molecular weight of about 35 to 50 kDa. More particularly, it can have a molecular weight of about 43 kDa.

DNA molecules encoding aforementioned imidazoline-receptive polypeptide(s) are also contemplated. Such a DNA molecule, e.g., a cDNA derived from mRNA, can contain a nucleotide sequence encoding the 651 amino acid sequence shown in SEQ ID No. 5. Thus, a DNA molecule containing the 1954 base pairs (b.p.) (1954 b.p. encodes 651 amino acids) nucleotide sequence shown in SEQ ID No. 2 is contemplated. This represents the coding sequence for the polypeptide predicted by EST04033 transfections. In another embodiment, a DNA molecule includes the longer nucleotide sequence shown in SEQ ID No. 3. This represents the cDNA predicted to have been translated+not predicted to have been translated in transfections experiments of EST04033.

In another embodiment of the invention, a DNA molecule contains a nucleic acid sequence encoding the amino acid sequence shown in SEQ ID No. 6. In another aspect, it can include the 1171 b.p. nucleic acid sequence shown in SEQ ID No. 4. The 1171 b.p. nucleic acid sequence shown in SEQ ID No. 4 is the 5A-1 non-plasmid DNA.

The nucleic acid sequence of the genomic clone encoding the imidazoline receptor is further shown in SEQ ID No. 21. The nucleic acid and amino acid sequence of the predicted transcript (ie., cDNA) can be predicted from the description hereinbelow. The polypeptide encoded by the genomic DNA is shown in SEQ ID No. 22.

Sequence similarity with the sequences indicated in SEQ ID protocols of the attached Sequence Listing is defined in connection with the present invention as a very close structural relationship of the relevant sequences with the sequences indicated in the respective SEQ ID protocols. To determine the sequence similarity, in each case the structurally mutually corresponding sections of the sequence of the SEQ ID protocol and of the sequence to be compared therewith are superimposed in such a way that the structural correspondence between the sequences is a maximum, account being taken of differences caused by deletion or insertion of individual sequence members (DNA-codon or amino acid respectively), and being compensated by appropriate shifts in sections of the sequences. The sequence similarity in % results from the number of sequence members which now correspond to one another in the sequences ("homologous positions") relative to the total number of members contained in the sequences of the SEQ ID protocols. Differences in the sequences may be caused by variation, insertion or deletion of sequence members. Additionally in DNA sequences, different DNA-codons encoding for the same amino acid are considered identical in the context of the present invention. For amino acid sequences, conservative amino acid substitutions encoded by their corresponding DNA-codons, as well as naturally occurring homologs of the sequences, are considered within the context of sequence similarity.

DNA molecules of substantial homology ($\geq 75\%$) are an implicit aspect of this sort of invention. As will be discussed later, the inventors have already identified two possible splice variants in the amino acid coding sequence. In addition, artificially mutated receptor cDNA molecules can be routinely constructed by methods such as site-directed polymerase chain reaction-mediated mutagenesis [Nelson and Long, *Anal. Biochem.* 180: 147–151 (1989)]. It is commonly appreciated that highly homologous mutants frequently mimic their natural receptor. A study by Kjelsberg et al. [J. Biol. Chem. 267: 1430–1433 (1992)]) showed that all 20 amino acid substitutions produce an active receptor at a single site in the $\alpha_{1b}$-adrenergic receptor. RNA molecules of $\geq 75\%$ complementarity to an instant DNA molecule, e.g., an mRNA molecule (sense) or a complementary cRNA molecule (antisense), are a further aspect of the invention.

A further aspect of the invention is for a recombinant vector, as well as a host cell transfected with the recombinant vector, wherein the recombinant vector contains at least one of the nucleotide sequences shown in SEQ ID Nos. 1–4, or sequences predicted by the genomic clone, or nucleotide sequences $\geq 75\%$ homologous thereto.

A method of producing an imidazoline receptor protein is another aspect of the invention. Such a method entails transfecting a host cell with an aforementioned vector, and culturing the transfected host cell in a culture medium to generate the imidazoline receptor.

A method for producing homologous imidazoline receptor proteins, and the proteins produced thereby, are also considered an aspect of this invention.

A significant further aspect of the invention is a method of screening for a ligand that binds to an imidazoline receptor. Such a method can comprise culturing an above-mentioned transfected cell in a culture medium to express imidazoline receptor proteins, followed by contacting the proteins with a labelled ligand for the imidazoline receptor under conditions effective to bind the labelled ligand thereto. The imidazoline receptor proteins can then be contacted with a candidate ligand, and any displacement of the labelled ligand from the proteins can be detected. Displacement of labelled ligand signifies that the candidate ligand is a ligand for the imidazoline receptor. These steps could be performed on intact host cells, or on proteins isolated from the cell membranes of the host cells.

The invention will now be described in more detail with reference to specific examples.

BRIEF DESCRIPTION OF THE DRAWINGS

FIG. 1 depicts a comparison of Reis antiserum (lane 1, 1:2000 dilution) and Dontenwill antiserum (lane 2, 1:5000 dilution) immunoreactivities for human NRL (same as RVLM) and hippocampus, as discussed in Example 1.

FIG. 2 depicts a comparison of Reis antiserum (1:15,000 dilution) and Dontenwill antiserum (1:20,000 dilution) immunoreactivities for plaques isolated from the human hippocampal cDNA library used in cloning as discussed in Example 2. The plaques contain the initial clone, designated herein as 5A-1, in a third stage of purification.

DETAILED DESCRIPTION OF THE INVENTION

Figure 3:
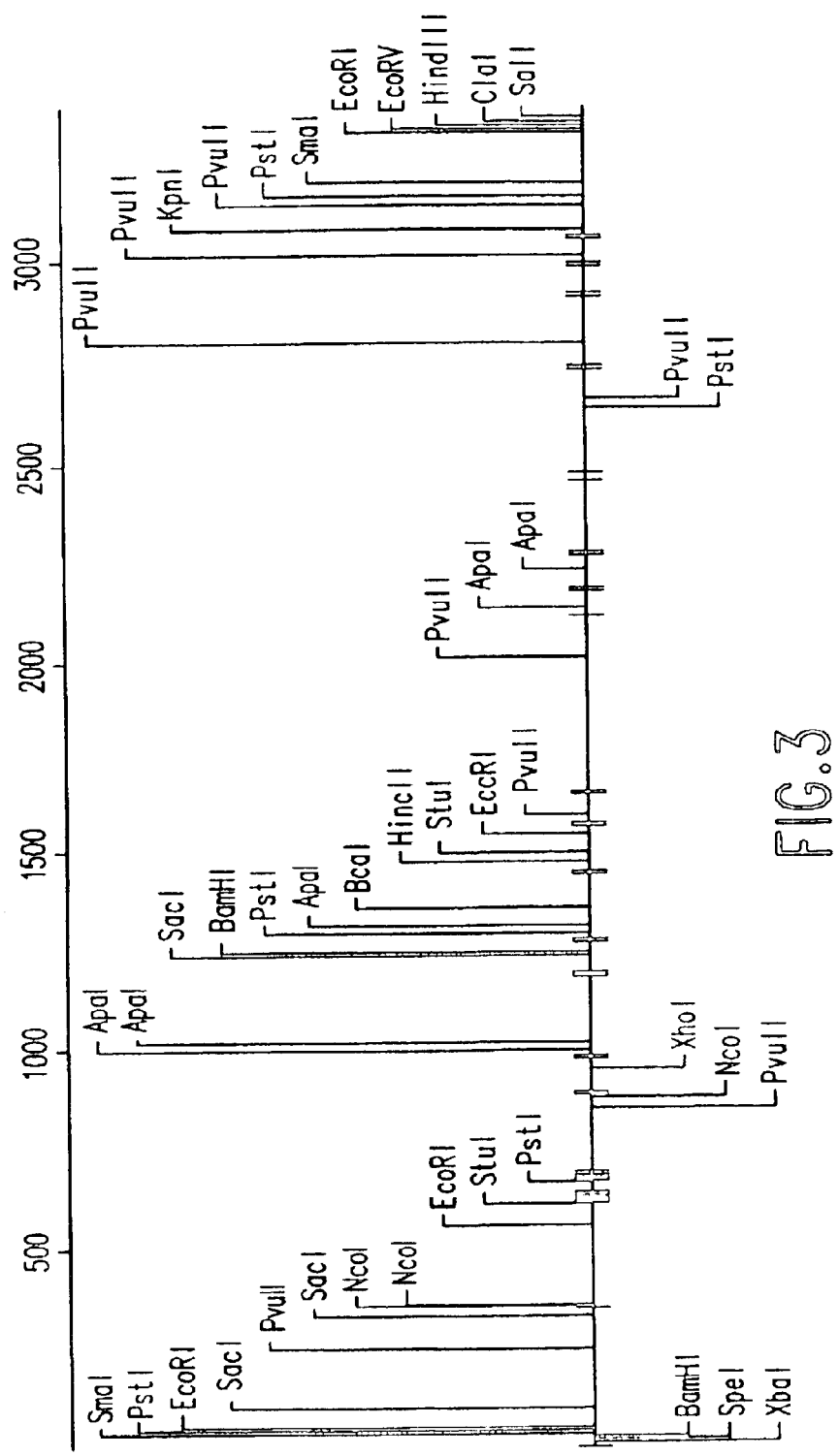
FIG. 3 depicts the restriction map of the EST04033 cDNA clone.

The present invention is concerned with multiple aspects of an imidazoline receptor protein, and DNA molecules encoding the same, and fragments thereof, which have now been discovered.

First, a polypeptide having imidazoline binding activity has been identified, which contains the putative active site for binding, as discussed hereinafter. Although polypeptide (s) described herein has a binding affinity for an imidazoline compound, it may also have an enzymatic activity, such as do catalytic antibodies and ribozymes. In fact, one such domain within our protein predicts a cytochrome p450 activity (described later).

Exemplary "binding" polypeptides are those containing either of the amino acid sequences shown in SEQ ID Nos. 5 or 6 (with the amino acid sequence predicted by EST04033 given in SEQ ID No. 5). Functionally equivalent polypeptides are also contemplated, such as those having a high degree of homology with such aforementioned polypeptides, particularly when they contain the Glu-Asp-rich region described hereinafter which we believe may define an active imidazoline binding site.

A polypeptide of the invention can be formed by direct chemical synthesis on a solid support using the carbodiimide method [R. Merrifield, *JACS*, 85: 2143 (1963)]. Alternatively, and preferably, an instant polypeptide can be produced by a recombinant DNA technique as described herein and elsewhere [e.g., U.S. Pat. No. 4,740,470 (issued to Cohen and Boyer), the disclosure of which is incorporated herein by reference], followed by culturing transformants in a nutrient broth.

Second, a DNA molecule of the present invention encodes aforementioned polypeptide. Thus, any of the degenerate set of codons encoding an instant polypeptide is contemplated. A particularly preferred coding sequence is the 1954 b.p. sequence set forth in SEQ ID No. 2, which has now been discovered to be a nucleotide sequence that encodes a polypeptide capable of binding imidazoline compound(s). In another embodiment, a DNA molecule includes the 3318 b.p. nucleotide sequence shown in SEQ ID No. 3. This latter sequence is the entire EST04033 insert. It includes the nucleotide sequence of SEQ ID No. 2 which was predicted to have been translated into protein in the transfection experiments.

In another embodiment of the invention, a DNA molecule contains a nucleic acid sequence encoding the amino acid sequence (390 residues) shown in SEQ ID No. 6. This amino acid sequence corresponds to that derived from direct sequencing of the 5A-1 clone and represents a fragment of the native protein. The 5A-1 DNA molecule is defined by the 1171 b.p. nucleic acid sequence shown in SEQ ID No. 4.

A DNA molecule of the present invention can be synthesized according to the phosphotriester method [Matteucci et al., JACS, 103: 3185 (1988)]. This method is particularly suitable when it is desired to effect site-directed mutagenesis of an instant DNA sequence, whereby a desired nucleotide substitution can be readily made. Another method for making an instant DNA molecule is by simply growing cells transformed with plasmids containing the DNA sequence, lysing the cells, and isolating the plasmid DNA molecules. Preferably, an isolated DNA molecule of the invention is made by employing the polymerase chain reaction (PCR) [e.g., U.S. Pat. No. 4,683,202 (issued to Mullis)] using synthetic primers that anneal to the desired DNA sequence, whereby DNA molecules containing the desired nucleotide sequence are amplified. Also, a combination of the above methods can be employed, such as one in which synthetic DNA is ligated to cDNA to produce a quasi-synthetic gene [e.g., U.S. Pat. No. 4,601,980 (issued to Goeddel et al.)].

A further aspect of the invention is for a vector, e.g., a plasmid, that contains at least one of the nucleotide sequences shown in SEQ ID Nos. 1–4 or those predicted by the genomic clone in SEQ ID No. 21. Whenever the reading frame of the vector is appropriately selected, the vector encodes an IR polypeptide of the invention. Hence, as well as full-length protein, fragments of the native IR protein are contemplated; as well as fusion proteins that incorporate an amino acid sequence as described herein. Also, a vector containing a nucleotide sequence having a high degree of homology with any of SEQ ID Nos. 1–4 or 21 is contemplated within the invention, particularly when it encodes a protein having imidazoline binding activity.

A recombinant vector of the invention can be formed by ligating an afore-mentioned DNA molecule to a preselected expression plasmid, e.g., with T4 DNA ligase. Preferably, the plasmid and DNA molecule are provided with cohesive (overlapping) terminii, with the plasmid and DNA molecule operatively linked (i.e., in the correct reading frame).

Another aspect of the invention is a host cell transfected with a vector of the invention. Relatedly, a protein expressed by a host cell transfected with such a vector is contemplated, which protein may be bound to the cell membrane. Such a protein can be identical with an aforementioned polypeptide, or it can be a fragment thereof, such as when the polypeptide has been partially digested by a protease in the cell. Also, the expressed protein can differ from an aforementioned polypeptide, as whenever it has been subjected to one or more post-translational modifications. For the protein to be useful within the context of the present invention, it should exhibit imidazoline binding capacity.

A method of producing an imidazoline receptor protein is another aspect of the invention, which entails transfecting a host cell with an aforementioned vector, and culturing the transfected host cell in a culture medium to generate the imidazoline receptor. The receptor molecule can undergo any post-translational modification(s), including proteolytic decomposition, whereby its structure is altered from the basic amino acid residue sequence encoded by the vector. A suitable transfection method is electroporation, and the like.

With respect to transfecting a host cell with a vector of the invention, it is contemplated that a vector encoding an instant polypeptide can be transfected directly in animals. For instance, embryonic stem cells can be transfected, and the cells can be manipulated in embryos to produce transgenic animals. Methods for performing such an operation have been previously described [Bond et al., Nature, 374:272–276 (1995)]. These methods for expressing an instant cDNA molecule in either tissue culture cells or in animals can be especially useful for drug discovery.

Possibly the most significant aspect of the present invention is in its potential for affording a method of screening for a ligand (drug) that binds to an imidazoline receptor. Such a method comprises culturing an above-mentioned host cell in a culture medium to express an instant imidazoline receptive polypeptide, then contacting the polypeptides with a labelled ligand, e.g., radiolabelled p-iodoclonidine, for the imidazoline receptor under conditions effective to bind the labelled ligand thereto. The polypeptides are further contacted with a candidate ligand, and any displacement of the labelled ligand from the polypeptides is detected. Displacement signifies that the candidate ligand actually binds to the imidazoline receptor. These steps could be performed on intact host cells, or on proteins isolated from the cell membranes of the host cells.

Typically, a suitable drug screening protocol involves preparing cells (or possibly tissues from transgenic animals) that express an instant imidazoline receptive polypeptide. In this process, categories of chemical structure are systematically screened for binding affinity or activation of the receptor molecule encoded by the transfected cDNA. This process is currently referred to as combinatorial chemistry. With respect to the imidazoline receptor, a number of commercially available radioligands, e.g., $^{125}$PIC, can be used for competitive drug binding affinity screening.

An alternative approach is to screen for drugs that elicit or block a second messenger effect known to be coupled to activation of the imidazoline receptor, e.g., moxonidine-stimulated arachidonic acid release. Even with a weak binding affinity or activation by one category of chemicals, systematic variations of that chemical structure can be studied and a preferred compound (drug) can be deduced as being a good pharmaceutical candidate. Identification of this compound would lead to animal testing and upwards to human trials. However, the initial rationale for drug discovery becomes vastly improved with an instant cloned imidazoline receptor.

Along these lines, a drug screening method is contemplated in which a host cell of the invention is cultured in a culture medium to express an instant imidazoline receptive polypeptide. Intact cells are then exposed to an identified agent (ie., agonist, inverse agonist, or antagonist) under conditions effective to elicit a second messenger or other detectable responses upon interacting with the receptor molecule. The imidazoline receptive polypeptides are then contacted with one or more candidate chemical compounds (drugs), and any modification in a second messenger response is detected. Compounds that mimic an identified agonist would be agonist candidates, and those producing the opposite response would be inverse agonist candidates. Those compounds that block the effects of a known agonist would be antagonist candidates for an in vivo imidazoline receptor. For meaningful results, the contacting step with a candidate compound is preferably conducted at a plurality of candidate compound concentrations.

A method of probing for another gene encoding an imidazoline receptor or homologous protein is further contemplated. Such a method comprises providing a radiolabelled DNA molecule identical or complementary to one of the above-described cDNA molecules (probe). The probe is then placed in contact with genetic material suspected of containing a gene encoding an imidazoline receptor or encoding a homologous protein, under stringent hybridization conditions (e.g., a high stringency wash condition is 0.1×SSC, 0.5% SDS at 65° C.), and identifying any portion of the genetic material that hybridizes to the DNA molecule.

Still further, a method of selectively producing antibodies, (e.g., monoclonal antibodies, immunoreactive with an instant imidazoline-receptive protein) comprises injecting a mammal with an aforementioned polypeptide, and isolating the antibodies produced by the mammal. This aspect is discussed in more detail in an example presented hereinafter.

The present inventors began their search for a human imidazoline receptor cDNA by screening a λgt11 phage human hippocampus cDNA expression library. Their research had indicated that both of the known antisera (Reis and Dontenwill) that are directed against human imidazoline receptors were immunoreactive with identical bands on SDS gels of membranes prepared from the human hippocampus (an in other tissues). By contrast, other brain regions either were commercially unavailable as cDNA expression libraries or yielded inconsistencies between the two antisera. Therefore, it was felt that a human hippocampal cDNA library held the best opportunity for obtaining a cDNA for an imidazoline receptor. Immunoexpression screening was chosen over other cloning strategies because of its sensitivity when coupled with the ECL detection system used by the present inventors, as discussed hereinbelow.

A number of unique discoveries led to identifying the first 5A-1 clone as an imidazoline receptor cDNA. These included discoveries that led to the choice of a hippocampal cDNA library and adapting ECL to the antisera. Once the initial clone (5A-1) was identified and sequenced, a more complete clone (EST04033) was purchased without restriction from ATCC Inc. (Catalogue # 82815; American Type Culture Collection, Rockville, Md.). EST 04033 was the only EST clone available at the time of the discovery of 5A-1, that contained a segment of complete homology (the origination of EST04033 is discussed later on). The binding affinities of the expressed protein after transfection in COS cells were determined by radioligand binding procedures developed in the inventor's laboratory [Piletz and Sletten, 1993, ibid].

To identify an instant cDNA clone encoding an imidazoline receptor it was preferable to employ both of the known antibodies to imidazoline receptors. These antibodies were obtained by contacting Dr. D. Reis (Cornell University Medical Center, New York City), and Drs. M. Dontenwill and P. Bousquet (Laboratoire de Pharmacologie Cardiovascular et Renale, CNRS, Strasbourg, France). These antisera were obtained free of charge and without confidentiality or restrictions on their use. The former antiserum (Reis antiserum) was derived from a published imidazoline receptor protein [Wang et al., (1992, 1993), the disclosures of which are incorporated herein by reference]. The method for raising the latter antiserum (Dontenwill antiserum) has also been published [Bennai et al., (1995), the disclosure of which is also incorporated herein by reference]. The latter antiserum was developed using an anti-idiotypic approach that identified the pharmacologically correct (clonidine and idazoxan selective) binding site structure.

EXAMPLE 1

Selectivity of the Antisera

The obtained Reis antiserum had been prepared against a purified imidazoline binding protein isolated from BAC cells, which protein runs in denaturing-SDS gels at 70 Kda [Wang et al., 1992, 1993]. The Dontenwill antiserum is anti-idiotypic, and thus is believed to detect the molecular configuration of an imidazoline binding site domain in any species. Prior to being used for screening plaques, both antisera were cleaned by stripping out possible antibacterial antibodies.

Both antisera have been tested to ensure that they are in fact selective for a human imidazoline receptor. In particular, we found that both of these antisera detected identical bands in human platelets and hippocampus; and in brainstem RVLM (NRL) by Western blotting (see FIG. 1). In these studies, in order to increase sensitivity over previously published detection methods, an ECL (Enhanced Chemiluminescence) system was employed. The linearity of response of the ECL system was demonstrated with a standard curve. ECL detection was demonstrated to be very quantifiable and about ten times more sensitive than other screening methods previously used with these antisera. Western blots with antiserum dilutions of 1:3000 revealed immunoreactivity with as little as 1 ng of protein from a human hippocampal homogenate by dot blot analysis.

For the studies depicted in FIG. 1, human hippocampal homogenate (30 μg) and NRL membrane proteins (10 μg) were electrophoresed through a 12.5% SDS-polyacrylamide gel, electrotransfered to nitrocellulose and sequentially incubated with (1) the Reis antibody (1:2000 dilution) and (2) the Dontenwill antibody (1:5000 dilution). Immunoreactive bands were visualized with an Enhanced Chemiluminescence (ECL) detection kit (Amersham) using anti-rabbit Ig-HRP conjugated antibody at a dilution of 1:3000 and the ECL detection reagents. Following detection with the antibody, blots were stripped and reprocessed omitting the primary antibody to check for complete removal of this antibody. In panels A and B, lane 1 shows the immunoreactive bands observed with the Reis antibody and lane 2 shows the bands detected with the Dontenwill antibody. Protein molecular weight standards are indicated to the left of each panel (in Kda).

Despite the diverse origins of the Reis and Dontenwill antisera, both of these antisera detected a similar 85 Kda protein in human brain and other tissues. But, a 33 Kda band was found in human platelets. Although the 33 Kda band is of smaller size than that reported for other tissues [Wang et al., 1993; Escriba et al., 1994; Greney et al., 1994], the fact that both antisera detected it, suggests that both the 85 Kda and 33 Kda bands may be imidazoline binding polypeptides. The 85 and 33 Kda bands were enriched in plasma membrane fractions, as is known to be the case for $IR_1$ binding, but not $I_2$ binding [Piletz and Sletten, 1993].

A significant positive correlation was established for the 85 Kda band detected by the Dontenwill antiserum with $IR_1$ Bmax values across nine rat tissues ($r^2=0.8736$). A similar positive correlation was established amongst platelet samples from 15 healthy platelet donors between radioligand $IR_1$ Bmax values (but not $I_2$ or $\alpha_2 AR$ Bmax values), and the 33 Kda band (presumed $IR_1$ immunoreactivity) on Western blots. This correlation exhibited a slope factor close to unity (results not shown). These correlations strongly suggested that an $IR_1$ binding protein might be revealed in an imidazoline receptor-antibody Western blotting assay. Furthermore, the Reis antiserum failed to detect authentic $\alpha_2 AR$, MAO A, or MAO B bands on gels, i.e., it was not immunoreactive with MAO at MW=61 Kda, or $\alpha_2 AR$ at MW=64 Kda. Additionally, no immunoreactive bands were observed using preimmune antiserum. Thus, after extensively characterizing these antisera with human and rat materials, it was concluded that these antisera are indeed selective for human imidazoline receptor protein.

EXAMPLE 2

Cloning of cDNA for an Imidazoline Receptor

A commercially available human hippocampal cDNA λgt11 expression library (Clontech Inc., Palo Alto, Calif.) was screened for immunoreactivity sequentially using both the anti-idiotypic Dontenwill antiserum and the Reis antiserum. Standard techniques to induce protein and transference to a nitrocellulose overlay were employed. [See, for instance, Sambrook et al., 1989, "Molecular Cloning: A Laboratory Manual," Cold Spring Harbor Laboratory Press]. After washing and blocking with 5% milk, the Dontenwill antiserum was added to the overlay at 1:20,000 dilution in Tris-buffered saline, 0.05% Tween 20, and 5% milk. The Reis antiserum was employed similarly, but at 1:15,000 dilution. These high dilutions of primary antiserum were chosen to avoid false positives. The secondary antibody was added, and positive plaques were identified using ECL. Representative results are shown in FIG. 2.

Positive plaques were pulled and rescreened until tertiary screenings yielded only positive plaques. Four separate positive plaques were identified from more than 300,000 primary plaques in our library. Recombinant λgt11 DNA purified from each of the four plaques was subsequently subcloned into E. coli pBluescript vector (Stratagene, La Jolla, Calif.). Sequencing of these four cDNA inserts in pBluescript demonstrated that they were identical, suggesting that only one cDNA had actually been identified four times. Thus, the screening had been verified as being highly reproducible and the frequency of occurrence was as expected for a single copy gene, i.e., one in 75,000 transcripts. As shown in FIG. 2, the protein produced by the first positive clone, designated 5A-1, tested positive with both the Reis antiserum and the Dontenwill antiserum. Clone 5A-1 has been deposited under the Budapest Treaty with the American Type Culture Collection (ATCC), 12301 Parklawn Drive, Rockville, Md., USA, 20852, on Aug. 28, 1997 and has been assigned deposit accession no. ATCC 209217. Tertiary-screened plaques of 5A-1 were all immuno-positive with either of the two known anti-imidazoline receptor antisera, but not with either preimmune antisera. These results suggested that clone 5A-1 encoded a fusion peptide similar to or identical with one of the predominant bands detected in human Western blots by both the Dontenwill and Reis antisera.

Sequencing of the first four clones was performed by contracting with ACGT Company (Chicago, Ill.) after subcloning them into pBluescript vector SK (Stratagene). Both manual and automatic sequencing strategies were employed which are outlined as follows:

Manual Sequencing

1. DNA sequencing was performed using T7 DNA polymerase and the dideoxy nucleotide termination reaction.
2. The primer walking method [Sambrook et al., ibid.] was used in both directions.
3. ($^{35}$S)dATP was used for labelling.
4. The reactions were analyzed on 6% polyacrylamide wedge or non-wedge gels containing 8 M urea, with samples being loaded in the order of A C G T.
5. DNA sequences were analyzed by MacVector Version 5.0. and by various Internet-available programs, i.e., the BLAST program.

Automatic Sequencing

1. DNA sequencing was performed by the fluorescent dye terminator labelling method using AmpliTaq DNA polymerase (Applied Biosystems Inc., Prizm DNA Sequencing Kit, Perkin-Elmer Corp., Foster City, Calif.).
2. The primer walking method was used. The primers actually used were a subset of those shown in SEQ ID Nos. 7–20.
3. Sequencing reactions were analyzed on an Applied Biosystems, Inc. (Foster City, Calif.) sequence analyzer.

These results demonstrated that the initial clone (5A-1) contained a 1171 base pair insert (see SEQ ID No. 4). The entire 5A-1 cDNA was found to exist as extended open reading frame for translation into protein. Consequently, it was determined that the 5A-1 cDNA must be a fragment of a larger mRNA.

cDNA Sequence Homologies

Using programs and databases available on the Internet (retrieved from NCBI Blast E-mail Server address blast@ncbi.nlm.nih.gov), it was determined that the 5A-1 clone encodes a previously undefined unique molecule. The BLASTP program [1.4.8 MP, 20 Jun. 1995 (build Nov. 13, 1995)] was used to compare all of the possible frames of amino acid sequences encoded by 5A-1 versus all known amino acid sequences available within multiple international databases [Altschul et al., *J. Mol. Biol.*, 215: 403–410 (1990)]. Only one protein, from *Micrococcus luteus*, possessed a marginally significant homology (p=0.04)(41%) over a short stretch of 75 of the 390 amino acids encoded by 5A-1. Otherwise, there were not any amino acid homologies (i.e., with p≦0.05) for any known proteins. Therefore, the protein encoded by 5A-1 is not significantly related to MAO A or B, $\alpha_2 AR$, or any other known eukaryotic protein in the literature.

In contrast to the amino acid search on BLASTP, two nearly homologous EST cDNA sequences of undefined nature covering 155 and 250 b.p. of the 5A-1 clone were reported to exist using BLASTN (reached from the same Internet server on Nov. 13, 1995). BLASTN is a program used to compare known DNA sequences from international databases, regardless of whether they encode a polypeptide. Neither of the two EST cDNA sequences having high homology to 5A-1, to our knowledge have been reported anywhere else except on the Internet. Both were derived as Expressed Sequence Tags (ESTs) in random attempts to sequence the human cDNA repertoire [as described in Adams et al., *Science*, 252: 1651–1656 (1991)]. As far as can be determined, the people who generated these ESTs lack any knowledge of what protein(s) they encode. One cDNA, designated HSA09H122, contained 250 b.p. with 7 unknown/incorrect base pairs (97% homology) versus 5A-1 over the same region. HSA09H122 was generated in France (Genethon, B. P. 60, 91002 Evry Cedex France) from a human lymphoblast cDNA library. The other EST, designated EST04033, contained 155 b.p. with 12 unknown/ incorrect base pairs (92% homology) versus 5A-1 over the same region. EST04033 was generated at the Institute for Genomic Research (Gaithersburg, Md.) from a human fetal brain cDNA clone (HFBDP28). Thus, both of these ESTs are short DNA sequences and contain a number of errors (typical of single-stranded sequencing procedures as used when randomly screening ESTs).

Based on the BLASTN search, the owner of HSA09H122 was contacted in an effort to obtain that clone. The current owner of the clone appears to be Dr. Charles Auffret (Paul Brousse Hospital, Genetique, B. P. 8, 94801 Villejuif Cedex, France). Dr. Auffret indicated by telephone that his clone came from a lot of clones believed to be contaminated with yeast DNA, and he did not trust it for release. Contamination with yeast DNA of that clone was later confirmed to have been reported within an Internet database. Thus, HSA09H122 was not reliable.

The other partial clone (EST04033) was purchased from American Type Culture Collection in Rockville, Md. (ATCC Catalog no. 82815). A telephone call to the Institute for Genomic Research revealed that it had been deposited at ATCC recently. As far as can be determined, the present inventors were the first to completely sequence EST04033. The complete size of EST04033 was 3385 b.p. (SEQ. ID No. 1), with a 3318 b.p. nonplasmid insert (see SEQ ID No. 3). Within this sequence of EST04033 the remaining 783 base pairs of the coding sequence presumed for a 70 kDa imidazoline receptor were predicted at the 5' side of 5A-1 (i.e., 783 coding nucleotides unique to EST04033+1171 coding nucleotides of 5A-1=1954 predicted total coding nucleotides; assuming b.p. # 1397–1400 in SEQ. No. 1 encodes the initiating methinine). The entire 1954 b.p. coding region for an ~70 kDa protein is shown in SEQ ID No. 2. The nucleotide sequence of EST04033 was determined in the same manner as described previously for the 5A-1 clone. The nucleotide sequence of the entire clone is shown in SEQ ID No. 1. In this sequence, an identical overlap was observed for the sequence obtained previously for the 5A-1 clone and the sequence obtained for EST04033. The 5A-1 overlap began at EST04033 b.p. 2,181 (SEQ. ID. No. 1) and continued to the end of the molecule (b.p. 3,351).

Conclusions About Our cDNA Clones cDNA of the present invention encode a protein that is immunoreactive with both of the known selective antisera for an imidazoline receptor, i.e., Reis antiserum and Dontenwill antiserum. Thus, an instant cDNA molecule produces a protein immunologically related to a purified imidazoline receptor and has the antigenic specificity expected for an imidazoline binding site. These antisera have been documented in the scientific literature as being selective for an "imidazoline receptor", which provides strong evidence that such an imidazoline receptor has indeed been cloned.

As mentioned, our instant cDNA sequence contains open reading frame distinct from any previously described proteins. Therefore, the encoded protein is novel, and it is unrelated to $\alpha_2$-adrenoceptors or monoamine oxidases. Small hydrophobic domains in the predicted amino acid sequence suggest that the protein is probably membrane bound as expected for an imidazoline receptor.

EXAMPLE 3

Cloning of a Human Gene

A pre-made genomic library of human placental DNA was purchased from Stratagene (La Jolla, Calif.) to screen for an IR gene by hybridization. The genomic library was constructed in Stratagene's vector λ FIX® II (catalog # 946206), and it was grown in XL1-Blue MRA (P2) host bacteria. It was titered to yield approximately 50,000 plaques per 137 mm plate. Lifts from six such plates were screened in duplicate by hybridization. The DNA probe used for screening was a 1.85 kb EcoR1 fragment from EST 04033 cDNA (uniquely related to our sequences based on the BLASTN). After the restriction digestion of EST 04033 DNA, the 1.85 kb fragment was extracted from an agarose electrophoresis gel, cleaned according to the GENECLEAN® III kit manual (BIO 101, Inc., P.O. Box 2284, La Jolla, Calif.), and radiolabeled with [$\alpha$-$^{32}$P]d-CTP according to Stratagene's Prime-It® II Random Primer Labeling Kit manual. Plaques were lifted onto 137 mm Duralon-UV™ membranes (Stratagene's catalog #420102), denatured, and cross-linked with Stratgene's UV-Stratalinker™ 1800. Hybridization was conducted under high stringency conditions: prehybridization=6×SSC, 1% SDS, 50% formamide, and 100 µg/ml of sheared, denatured salmon sperm DNA at 42° C. for 2 hrs; hybridization=6×SSC, 1% SDS, 50% formamide, and 100 µg/ml of sheared, denatured salmon sperm DNA at 45° C. overnight; wash=2 washes of 1×SSC, 0.1% SDS at 65° C. and 3 washes of 0.2×SSC, 0.2% SDS at 65° C. This hybridization procedure is essentially described in Stratagene's vector λ FIX® II instruction manual. Positive plaques were localized by developing Kodak BioMax films. Two positive genomic clones of identical size were retained through three rounds of screening.

One of the positive genomic clones (designated JEP 1-A) was selected for complete characterization. It was found to contain an ≈17 kb insert. Large-scale preparations of this genomic clone DNA were performed using the λ QUICK! SPIN kit (BIO101, La Jolla, Calif.). To verify that we had cloned a gene corresponding to 5A-1 and EST04033 cDNA, some restriction site positions in the genomic clone were determined using the FLASH Nonradioactive Gene Mapping Kit (Stratagene) and compared to Southern blots of human DNA. The location of genomic sequences highly related to (or identical to) those of our cDNA clones was determined by high stringency hybridization (as above) with the following $^{32}$P-labeled probe: a 1110 bp ApaI-EcoR1 fragment from the cDNA clone 5A-1. This fragment was chosen as the probe because it lacks the GAG repeat (encoding glutamic acids), which might have complicated matters if it were found to be repeated elsewhere in the genome. With genomic clone JEP1-A, we detected a 14.1 kb EcoRI fragment and a 7.7 kb SacI fragment that hybridized with this probe. Southern blots containing EcoRI- or SacI-digested human genomic DNA (from human blood) with the 1110 bp ApaI-EcoRI cDNA probe also resulted in the detection of a 14.1 kb EcoRI fragment and a 7.7 kb SacI fragment. No additional restriction fragments of human genomic DNA appeared to hybridize with this probe under lower stringency conditions. These results strongly suggested that this gene (JEP-1A) encodes transcript(s) giving rise to the 5A-1 and EST04033 cDNA clones. Clone JEP-1A has been deposited under the Budapest Treaty with the American Type culture Collection (ATCC), 12301 Parklawn Drive, Rockville, Md., USA, 20852, on Aug. 28, 1997 and has been assigned deposit accession no. ATCC 209216.

Genomic DNA sequencing was done by contract with Cadus Pharmaceutical Corporation (Tarrytown, N.Y.). The original lambda JEP1-A clone was subcloned into pZero (Invitrogen) as a convenient vector. The initial fragments for sequencing were derived from Sac I and Xba I restriction enzymes. The short Sac I fragments of 1.5, 3.0 and 3.5 kb were further digested with Hind III, Pst I, and Kpn I yielding 15 subclones of varying length. The procedure consisted of sequencing all these subclones and parent clones with vector forward and reverse primers. Subsequently, this initial round of sequencing was supplemented with primer walking using custom oligonucleotides. The Sac I fragments were joined together by primer walking using the 2 Xba I fragments of 3 and 10 Kb. Then, the largest Sac I fragment (8 kb) and the 10 kb Xba I fragment were used as templates for a transposon sequencing method. The method used was the Primer Island Transposition Kit (Perkin-Elmer Corp., Norwalk, Conn.; Applied Biosystems) (ABI). The kit consists of a synthetic transposon (Ty1) containing forward and reverse primers and the integrase enzyme which inserts the transposon randomly into the target plasmid DNA. Transposon insertion is an alternative to subcloning or primer walking when sequencing a large region of DNA (Devine and Boeke, Nucleic Acids Res. 22: 3765–3772 (1994); Devine et al., Genome Res., in press, (1997); Kimmel et al., In Genome Analysis., a Laboratory Manual, Cold Spring Harbor Press, NY, N.Y., in press (1997). A total of over 250 individual sequencing reactions were performed. Sequencing was done on ABI model 373 and 377 automated sequencers using ABI dye-terminator sequencing kits. Primers were designed using Gene Runner software (Hastings Software, Hastings On Hudson, N.Y.). Oligonucleotides were purchased from Gibco-BRL (Gaithersburg, Md.). Sequence assembly was performed using Sequencer Software (Gene Codes Corp., Ann Arbor, Mich.) from 4-fold redundancy of sequences.

Figure 5:
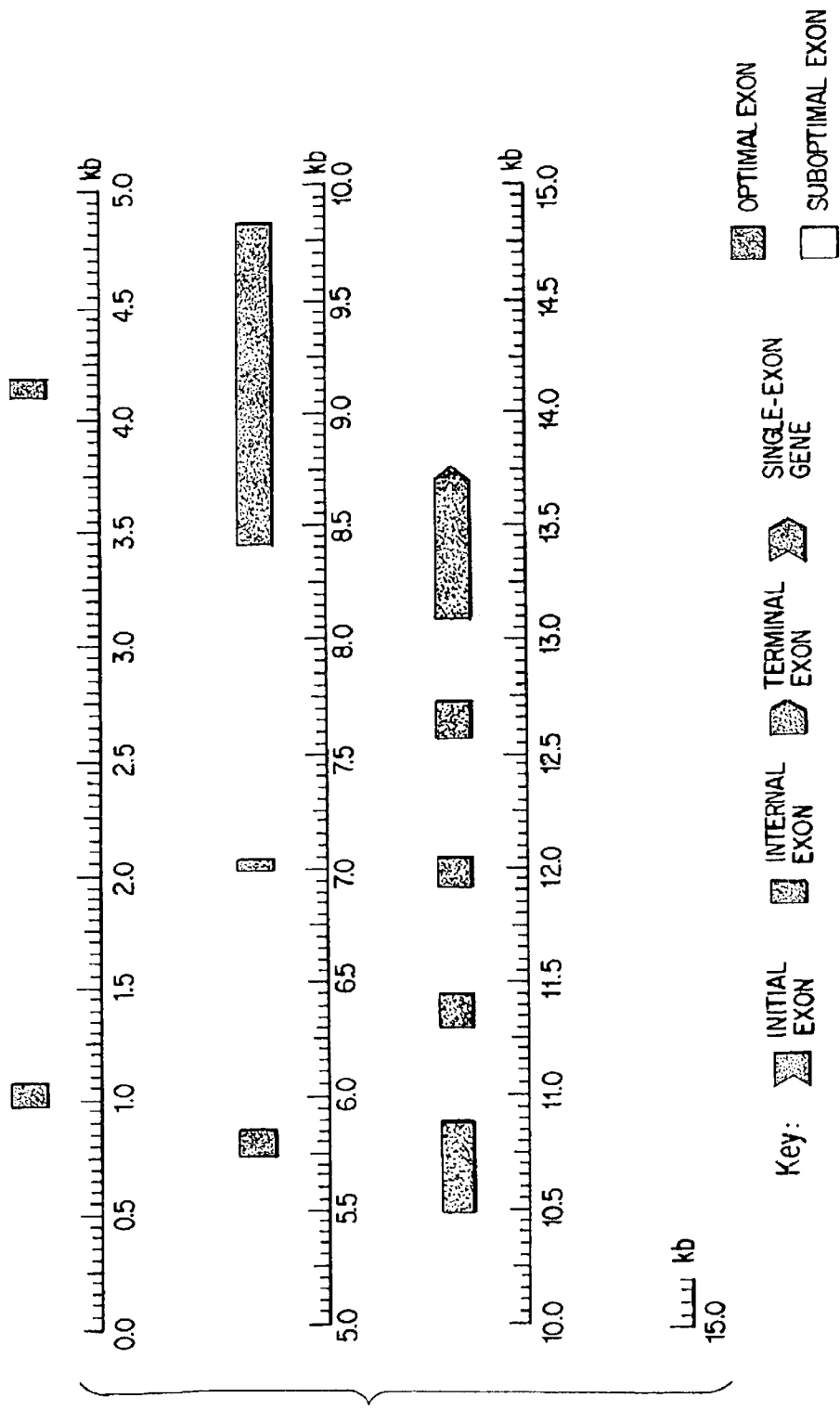
FIG. 5 depicts the prediction of introns and exons of the genomic clone (as analyzed by the GENESCAN program and verified by the available cDNAS).

The entire sequence of our JEP-1A genomic clone is shown in SEQ. 21. The computer program, GENSCAN 1.0, was able to identify splice sites of known topology. As expected, this gene contained a number of introns. See Table 1 hereinbelow. Only one continuous open reading frame was identified within our genomic clone. This open reading frame was interrupted by a number of introns (which is typical of eukaryotic transcripts) as shown in FIG. 5. The predicted polypeptide is encoded by the genomic DNA beginning at b.p. # 971 of SEQ ID No. 21. The predicted amino acid sequence of the polypeptide encoded thereby is shown in SEQ ID No. 22. As can be seen, the entire 5A-1 DNA and polypeptide sequence was encapsulated within this predicted genomic transcript. Therefore, there is no question that this is the gene encoding 5A-1 and EST04033 cDNA. In addition, JEP-1A has more nearly defined the full-length transcript (by at least 102 more coding nucleotides than the cDNAs alone).

A BLASTN analysis of the entire genomic sequence (on Aug. 26, 1997) demonstrated again that this gene has not been previously defined in the literature.

As with the cDNA clones, some EST sequences of identity were found (listed below and later). Of particular interest was a variance in the first intron splice site predicted by the computer. Upstream of that site (ie., upstream of amino acids PEKKGGE=amino acids predicted after first splice site) we have identified two types of transcripts. Genomic clone JEP-1A predicted 34 amino acids upstream of that sequence before entering another intron upstream. In an identical manner, three ESTs (H61282, AA428790 and AA428250) overlapped that entire region in our clones and they contained the identical nucleotides for those 34 amino acids, plus an additional 22 more amino acids further upstream. By comparison, however, our EST04033 varied from all of these ESTs upstream of that site. This means, the first 1,532 nucleotides of EST04033 (thought to encode translation of amino acids 1–56 of EST04033 beginning at b.p. 1,398 in SEQ. 1) are completely at variance with the other ESTs down to that splice site, but from there on they are identical. This provides strong evidence that this site can generate two alternatively spliced transcripts which can produce at least one functional protein (ie., the transfections with EST04033). For the reader's information, this splice site is upstream of b.p. # 1,565 in SEQ. 1, b.p. # 168 in SEQ. 2, b.p. # 1,532 in SEQ. 3, amino acid # 57 in SEQ. 5, and b.p. # 971 in the genomic SEQ. 21.

Genomic Sequence Analysis

Of interest is a unique glutamic- and aspartic acid-rich region within our predicted protein. This region of the IR protein delineates a highly unique span of 59 amino acids, 36 of which are Glu or Asp residues (61%). This region was largely discovered within clone 5A-1 and it is present within all discovered and predicted transcripts from the gene (EST04033 included). This sequence lies between two potential transmembrane loops (hydrophobic domains). The identification of this unique Glu/Asp-rich domain within our clones is consistent with an expected negatively charged pocket capable of binding clonidine and agmatine, both of which are highly positively charged ligands. Also, since the Dontenwill antiserum was specifically developed against an idazoxan/clonidine binding site, and its immunoreactivity is directed against the clone 5A-1/λgt11 fusion protein, this suggests that clone 5A-1 might encode an imidazoline binding site. Furthermore, this glu/asp-rich sequence is

TABLE 1

Position of Predicted Introns and Exons

GENSCAN 1.0    Date run: Aug. 26, 1997    Time: 12:35:39
Sequence gs_seqfile:15202 bp:58.36% C + G:Isochore 4 (57.00–100.00 C + G %)
Parameter matrix: HumanIso.smat
Predicted genes/exons:

| Gn.Ex | Type | S | .Begin | ...End | .Len | Fr | Ph | I/Ac | Do/T | CodRg | P.. | Tscr.. |
|---|---|---|---|---|---|---|---|---|---|---|---|---|
| 1.01 | Intr | + | 971 | 1084 | 114 | 1 | 0 | 69 | 98 | 200 | 0.836 | 20.91 |
| 1.02 | Intr | + | 4096 | 4177 | 82 | 0 | 1 | 37 | 53 | 81 | 0.358 | -0.13 |
| 1.03 | Intr | + | 5732 | 5856 | 125 | 0 | 2 | 117 | 95 | 84 | 0.953 | 13.48 |
| 1.04 | Intr | + | 6997 | 7046 | 50 | 0 | 2 | 95 | 116 | 44 | 0.998 | 6.52 |
| 1.05 | Intr | + | 8416 | 9825 | 1410 | 1 | 0 | 96 | 94 | 2914 | 0.970 | 283.09 |
| 1.06 | Intr | + | 10489 | 10897 | 409 | 1 | 1 | 15 | 59 | 318 | 0.517 | 17.19 |
| 1.07 | Intr | + | 11293 | 11449 | 157 | 0 | 1 | 57 | 61 | 236 | 0.998 | 18.57 |
| 1.08 | Intr | + | 11923 | 12051 | 129 | 2 | 0 | 84 | 63 | 224 | 0.997 | 21.34 |
| 1.09 | Intr | + | 12570 | 12731 | 162 | 1 | 0 | 95 | 80 | 229 | 0.996 | 23.94 |
| 1.10 | Term | + | 13090 | 13700 | 611 | 2 | 2 | 59 | 41 | 1012 | 0.942 | 89.44 |
| 1.11 | PlyA | + | 14257 | 14262 | 6 | | | | | | | 1.05 | located within the longest stretch of homology that the clone has with any known protein, i.e., the ryanodine receptor (as determined by on BLASTN). Specifically, we have discovered four regions of homology between the imidazoline receptor and the ryanodine receptor, which are all Glu/Asp-rich. The total nucleic acid homology is 67% with the ryanodine receptor DNA over the stretches encompassing this region. However, this is not sufficient to indicate that the imidazoline receptor is a subtype of the ryanodine receptor, because this homologous stretch is still a minor portion of the overall transcript(s) identified in the gene. Instead, this significant homology may reflect a commonality in function between this region of the IR and the ryanodine receptor.

The Glu/Asp-rich region within the ryanodine receptor has also been reported to define a calcium and ruthenium red dye binding domain that modulates the ryanodine receptor/$Ca^{++}$ release channel located within the sarcoplasmic reticulum. The only other charged amino acids within the Glu/Asp-rich region of our clones are two arginines (the ryanodine receptor has uncharged amino acids at the corresponding positions).

Based on this identification of Arg residues within the Glu/Asp-rich region of the predicted imidazoline binding site, the assistance of Dr. Paul Ernsberger (Case Western Reserve University, Cleveland, Ohio) was enlisted. Dr. Ernsberger performed phenylglyoxal attack of arginine on native PC-12 membranes. Dr. Ernsberger was able to demonstrate that this treatment completely eliminated imidazoline binding sites in these membranes. This provides some indirect evidence that the native imidazoline binding site also contains an Arg residue. On the other hand, attempts to chemically modify cysteine and tyrosine residues, which are not located near the Glu/Asp-rich region did not affect PC-12 membrane binding of imidazolines.

As a further test of the sequence, it was determined whether native IR binding sites in PC-12 cells would be sensitive to ruthenium red. From the structure of the cloned sequence, it was reasoned that native IR should bind ruthenium red. Accordingly, a competition of ruthenium red with $^{125}$PIC at native IR sites on PC-12 membranes was studied. In these studies it was observed that ruthenium red competed for $^{125}$PIC binding to the same extent as did the potent imidazoline compound, moxonidine, i.e., 100% competition. Furthermore, the $IC_{50}$ for competition of ruthenium red at IR was slightly more robust than reported for ruthenium red on the activation of calcium-dependent cyclic nucleotide phosphodiesterase—the previous most potent effect of ruthenium red on any biological site—indicating possible pharmacological importance. It is also noteworthy that calcium failed to compete or $^{125}$PIC binding at PC-12 IR sites (as did a calcium substitute, lanthanum). We and others have previously reported that a number of other cations robustly interfere with IR binding [Ernsberger et al., *Annals NY Acad. Sci.*, 763: 22–42 (1995); Ernsberger et al., *Annals NY Acad. Sci.*, 763: 163–168 (1995)]. Attempts were also made to directly stain the proteins in SDS gels with ruthenium red [Chen and MacLennan, J. Biol. Chem., 269: 22698–22704 (1994)]. It was found that ruthenium red stains the same platelet (33 kDa) and brain (85 kDa) bands that Reis antiserum detects. (Remember, the same 33 kDa band was verified to directly correlate with $^{125}$PIC Bmax values for IR.) Thus, these results linked the attributes predicted from the cloned sequence to a native IR binding site.

Two other facets of the predicted polypeptide from JEP-1A suggest that we have identified most of the functional sequences. First, our predicted protein is comparable in regard to both the order and size of three regions of importance to the function of the interleukin-2Rβ receptor (IL-2Rβ1). Specifically, IL-2Rβ possesses the following regions over a span of 286 amino acids: ser-rich region, followed by glu/asp-rich region, followed by proline-rich region. Likewise, our predicted protein has the same three regions, in the same order, over a span of about 625 amino acids. This suggests that our protein might function similarly as cytokine receptors. Secondly, our predicted protein possesses a cytochrome p450 heme-iron ligand signature sequence [Nelson et al., Pharmacogenetics 6: 1–42 (1996)]. This suggests that our protein might also function as do cytochrome p450s in oxidative, peroxidative and reductive metabolism of endogenous compounds.

Some additional findings about the amino acid sequence of our instant IR polypeptide are: (1) The glu/asp-rich region also bears similarity to an amino acid sequence within a GTPase activator protein. (2) There appear to be four small hydrophobic domains indicative of transmembrane domain receptors. (3) A number of potential protein kinase C (PKC) phosphorylation sites appear near to the carboxy side of the protein, and we have previously found that treatment of membranes with PKC leads to an enhancement of native IR binding. Thus, these observations are all consistent with other observations expected for native IR.

RNA Studies

Figure 6A:
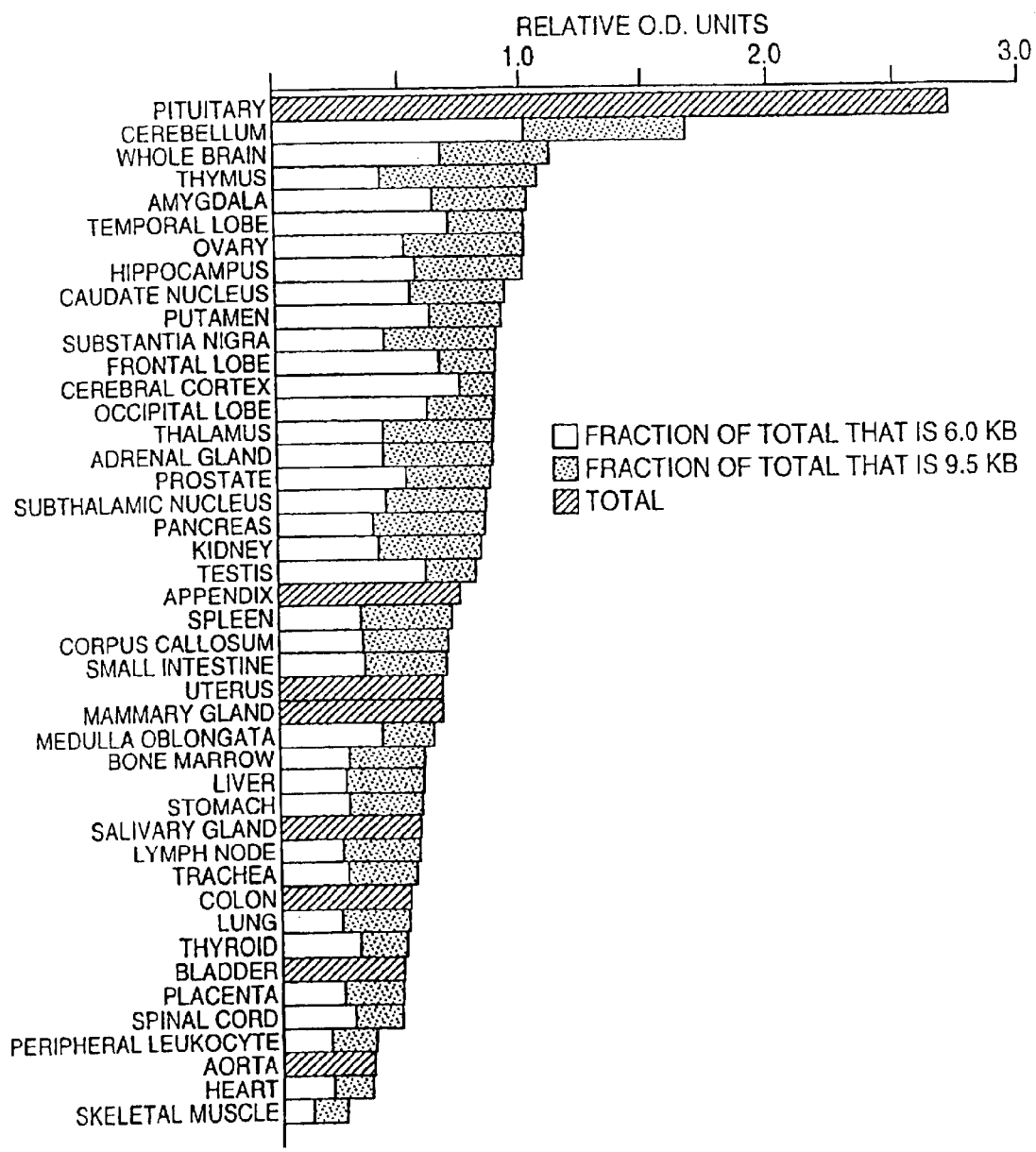
FIG. 6 depicts the distribution of mRNA homologous to our CDNA in human adult tissues (bar graph) and the two species of MRNA (6 and 9.5 kb).
Figure 6B:
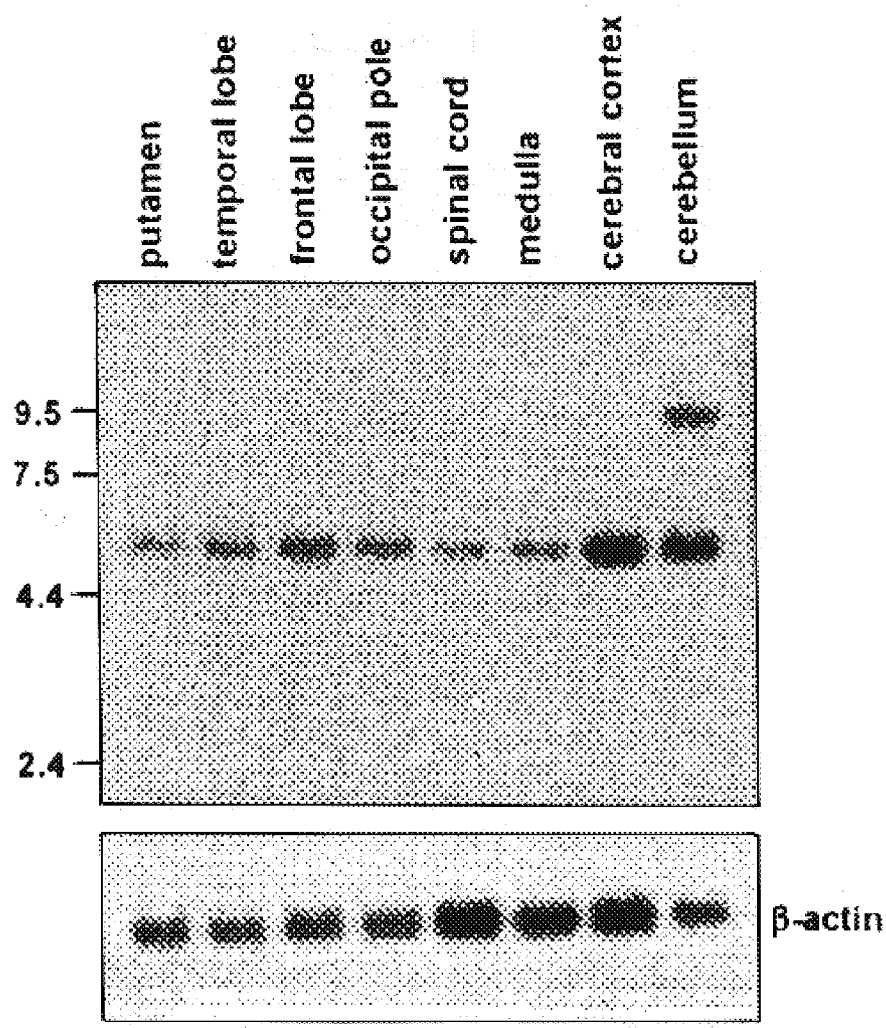

Northern blotting has also been performed on polyA$^+$ mRNA from human tissues in order to ascertain the regional expression of the mRNA corresponding to our cDNA. The same 1110 b.p. ApaI-EcoRI fragment from cDNA clone 5A-1 used in Southern blots was used for these studies. This probe region was not found within any other known sequences on the BLASTN database. The results revealed a 6 kb mRNA band, which predominated over a much fainter 9.5 kb mRNA in most regions (FIG. 6). Some exceptions to this pattern were in lymph nodes and cerebellum (FIG. 6), where the 9.5 kb band was equally or more intense. Although the 6 kb band is weakly detectable in some non-CNS tissues, it is enriched in brain. An enrichment of the 6 kb mRNA is observed in brainstem, although not exclusively. The regional distribution of the mRNA is somewhat in keeping with the reported distribution of IR binding sites, when extrapolated across species (FIG. 6). Thus, the rank order of Bmax values for IR in rat brain has been reported to be frontal cortex>hippocampus>medulla oblongata>cerebellum [Kamisaki et al., *Brain Res.*, 514: 15–21 (1990)]. Therefore, with the exception of human cerebellum, which showed two mRNA bands, the distribution of the mRNA for our the present cloned cDNA is consistent with it belonging to IR.

[It should be noted that while IR binding sites are commonly considered to be low in cerebral cortex compared to brainstem, this is in fact a misinterpretation of the literature based only on comparisons to the alpha-2 adrenoceptor's Bmax, rather than on absolute values. Thus, IR Bmax values have actually been reported to be slightly higher in the cortex than the brainstem, but they only "appear" to be low in the cortex in comparison to the abundance of alpha-2 binding sites in cortex. Therefore, the distribution of the IR mRNA is reasonably in keeping with the actual Bmax values for radioligand binding to the receptor [Kamisaki et al., (1990)].

A final point to emphasize about the Northern blots is that they clearly demonstrate two high-stringency transcripts (FIG. 6). This is in keeping with the alternatively spliced EST cDNAs mentioned earlier. Thus, we suggest this may be the basis for both the 6 and 9.5 kb transcripts.

Summary of Genomic Sequence Results

The JEP-1A clone clearly contains most of the gene. Within it we have identified at least 3,776 nucleotides for transcript(s) (encoding 1,065 amino acids plus 587 b.p. of untranslated region down to the polyT+ tail). This has been lengthened by at least 66 coding nucleotides upstream (22 amino acids) in comparison to overlapping ESTs. In addition to this, we are quite confident of the splice site for the two observed mRNA sizes. Most of the functional sequences are predicted to be encoded within our genomic clone.

A summary of the evidence that a gene encoding an imidazoline receptor protein has been cloned is summarized in Table 2 hereinbelow.

TABLE 2

Comparison of Protein Predicted From Our Clones with Properties of Native $IR_1$ and $I_2$ sites

| Imidazoline Receptor-like Clone | Authentic $IR_1$ | Authentic $I_2$ |
|---|---|---|
| Original λ phage fusion protein (from 5A-1) is immunoreactive with Dontenwill and Reis antibodies | Dontenwill-Ab activity (a) inhibits RVLM $IR_1$ binding ($^3$H-Clonidine), & (b) correlates with 85 kDa Western band. Reis-Ab activity correlates w platelet $IR_1$ Bmax ($^{125}$PIC binding) | Dontenwill & Reis Abs both inhibit brain $I_2$ sites ($^3$H-IDX). |
| Segment homologous to a GTPase-activator prot'n Predicts ≥ 120,000 MW protein | Weak to moderate sensitivity to GTP 85,000 MW immunoreactivity | Not sensitive to GTP 59–61,000 MW photoaffinity |
| Predicts 1–4 hydrophobic domains | Enriched in plasma membranes | Enriched in mitochondria |
| Encodes Glu/Asp-rich (negatively charged) domain consistent with $Ca^{++}$ and ruthenium red binding | Binds (+)-charged imidazolines Sensitive to divalent cations Sensitive to ruthenium red | Binds (+)-charged imidazolines Not sensitive to divalent cations Unknown sensitivity for Ruthen. red |
| Arginine is only positively charged amino acid near Glu/Asp domain | Arg attack eliminates binding Cys & Tyr attack w/o effect on binding | Unknown |
| Encodes PKC sites | PKC treatment enhances binding | Unknown |
| Human mRNA Distribution; F.Cortex > hippocampus > medulla | Rat $IR_1$ Bmax ($^{125}$PIC): F.Cortex > hippocampus > medulla | Rat $I_2$ Bmax ($^3$H-IDX): Medulla > F.Cortex |
| Transfected COS-7 cells expressed high affinity for moxonidine & p-iodoclonidine (PIC) | High affinity for moxonidine and PIC | Low affinity for moxonidine and PIC |

EXAMPLE 4

Transient Transfection Studies

COS-7 cells were transfected with a vector containing EST04033 cDNA, which was predicted based on sequence analysis to contain the glu/asp rich region thought to be important for ligand binding to the imidazoline receptor protein. The EST04033 cDNA was subcloned into pSVK3 (Pharmacia LKB Biotechnology, Piscataway, N.J.) using standard techniques [Sambrook, supra], and transfected via the DEAE-dextran technique as previously described [Choudhary et al., Mol. Pharmacol., 42: 627–633 (1992); Choudhary et al., Mol. Pharmacol., 43: 557–561 (1993); Kohen et al., J. Neurochem., 66: 47–56 (1996)]. A restriction map of the EST04033 cDNA is shown in FIG. 3. The restriction enzymes Sal I and Xba I were used for subcloning into pSVK3.

Briefly stated, COS-7 cells were seeded at $3 \times 10^6$ cells/100 mm plate, grown overnight and exposed to 2 ml of DEAE-dextran/plasmid mixture. After a 10–15 min. exposure, 20 ml of complete medium (10% fetal calf serum; 5 μg/ml streptomycin; 100 units/ml penicillin, high glucose, Dulbeccos' modified Eagle's medium) containing 80 μM chloroquine was added and the incubation continued for 2.5 hr. at 37° C. in a 5% $CO_2$ incubator. The mixture was then aspirated and 10 ml of complete medium containing 10% dimethyl sulfoxide was added with shaking for 150 seconds.

Following aspiration, 15 ml of complete medium with dialyzed serum was added and the incubation continued for an additional 65 hours. After this time period, the cells from 6 plates were harvested and membranes were prepared as previously described [Ernsberger et al., Annals NY Acad. Sci., 763: 22–42 (1995), the disclosure of which is incorporated herein by reference].

Parent, untransfected COS-7 cells were prepared as a negative control. Some membranes were treated with and without PKC for 2 hrs prior to analysis, since previous studies had indicated that receptor phosphorylation could be beneficial to detect IR binding.

Transfected samples were also analyzed by Western blots. The protocol used for Western blot assay of transfected cells is as follows. Cell membranes were prepared in a special cocktail of protease inhibitors (1 mM EDTA, 0.1 mM EGTA, 1 mM phenylmethyl-sufonylfluoride, 10 mM ε-aminocaproic acid, 0.1 mM benzamide, 0.1 mM benzamide-HCl, 0.1 mM phenanthroline, 10 μg/ml pepstatin A, 5 mM iodoacetamide, 10 μg/ml antipain, 10 μg/ml trypsin-chymotrypsin inhibitor, 10 μg/ml leupeptin, and 1.67 μg/ml calpain inhibitor) in 0.25 M sucrose, 1 mM $MgCl_2$, 5 mM Tris, pH 7.4. Fifteen μg of total protein were denatured and separated by SDS gel electrophoresis. Gels were equilibrated and electrotransferred to nitrocellulose membranes. Blots were then blocked with 10% milk in Tris-buffered saline with 0.1% Tween-20 (TBST) during 60 min. of gentle rocking. Afterwards, blots were incubated in anti-imidazoline receptor antiserum (1:3000 dil.) for 2 hours. Following the primary antibody, blots were washed and incubated with horseradish peroxidase-conjugated anti-rabbit goat IgG (1:3000 dil.) for 1 hr. Blots were extensively washed and incubated for 1 min. in a 1:1 mix of Amersham ECL detection solution. The blots were wrapped in cling-film (SARAN WRAP) and exposed to Hyperfilm-ECL (Amersham) for 2 minutes. Quantitation was based on densitometry using a standard curve of known amounts of protein containing BAC membranes or platelet membranes run in each gel.

One nM [$^{125}$I]p-iodoclonidine was employed in the radioligand binding competition assays, since at this low concentration this radioligand is selective for the IR site much more than for $I_2$ binding sites. The critical processes of membrane preparation of tissue culture cells and the radioligand binding assays of IR and $I_2$ have been reviewed by Piletz and colleagues [Ernsberger et al., Annals NY Acad. Sci., 763: 510–519 (1995)]. Total binding (n=12 per experiment) was determined in the absence of added competitive ligands and nonspecific binding was determined in the presence of $10^{-4}$ M moxonidine (n=6 per experiment). Log normal competition curves were generated against unlabeled moxonidine, p-iodoclonidine, and (−) epinephrine. Each concentration of the competitors was determined in triplicate and the experiment was repeated thrice.)

The protocol to fully characterize radioligand binding in the transfected cells entails the following. First, the presence of IR and/or $I_2$ binding sites are scanned over a range of protein concentrations using a single concentration of $[^{125}I]$-p-iodoclonidine (1.0 nM) and $^3H$-idazoxan (8 nM), respectively. Then, rate of association binding experiments (under a 10 μM mask of NE to remove $α_2AR$ interference) are performed to determine if the kinetic parameters are similar to those reported for native imidazoline receptors [Ernsberger et al. *Annals NY Acad. Sci.*, 763: 163–168 (1995]. Then, full Scatchard plots of $[^{125}I]$-p-iodoclonidine (2–20 nM if like IR) and $^3H$-idazoxan (5–60 nM if like $I_2$) binding are conducted under a 10 μM mask of NE. Total NE (10 μM)-displaceable binding is ascertained as a control to rule out $α_2$-adrenergic binding. The Bmax and $K_D$ parameters for the transfected cells are ascertained by computer modeling using the LIGAND program [McPherson, G., *J. Pharmacol. Meth.*, 14: 213–228 (1985)] using 20 μM moxonidine to define IR nonspecific binding, or 20 μM cirazoline to define $I_2$ nonspecific binding.

Figure 4:
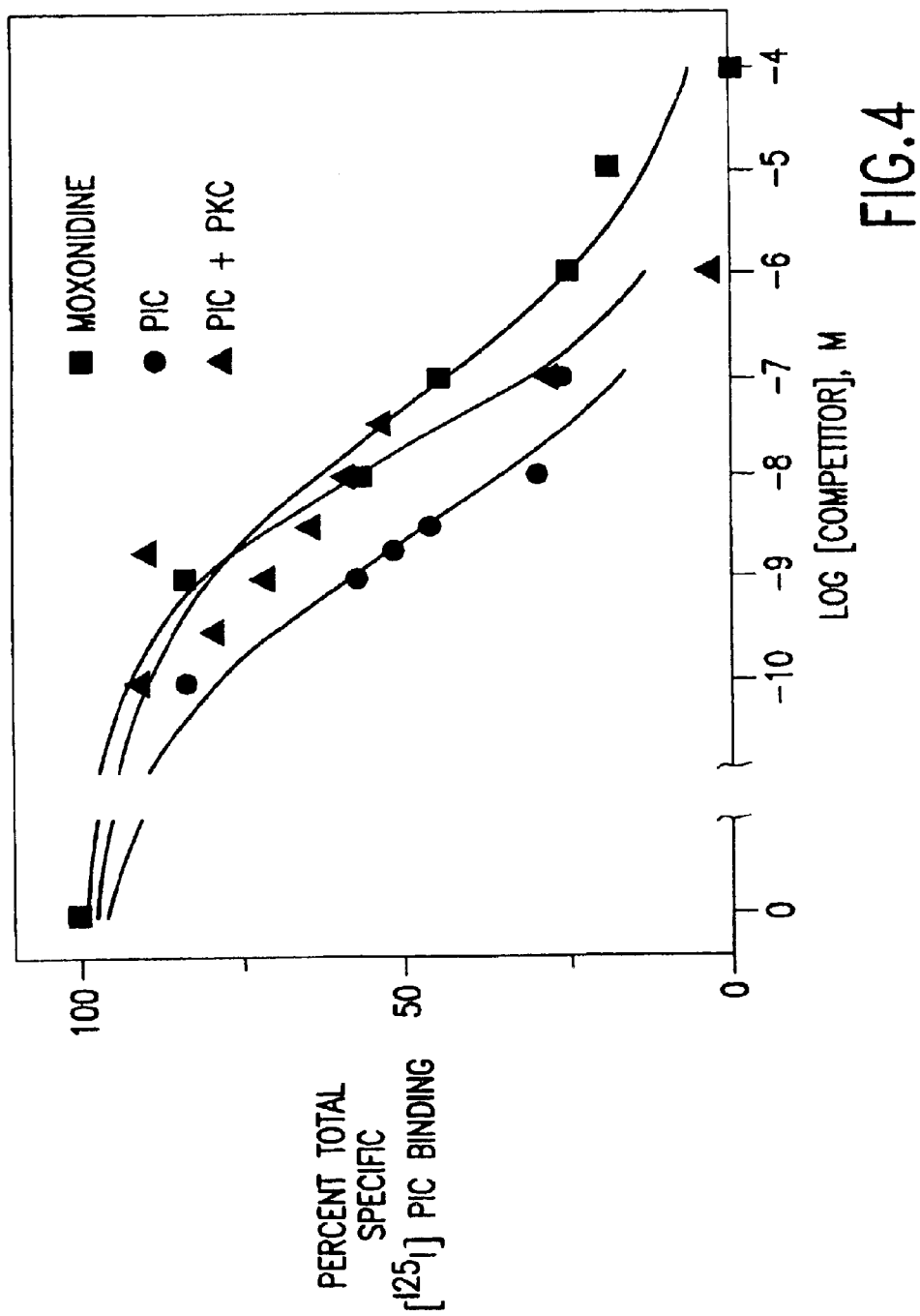
FIG. 4 depicts a competitive binding assay between $^{125}$I-labelled p-iodoclonidine (PIC) and various ligands for the imidazoline receptor on membranes expressed in COS cells transfected with the EST04033 cDNA clone, as discussed in Example 4.

The results of the transient transfection experiments of the imidazoline receptor vector into COS-7 cells are shown in FIG. 4. Competition binding experiments were performed using membrane preparations from these cells and $^{125}PIC$ was used to radiolabel IR sites. A mask of 10 μM norepinephrine was used to rule out any possible $α_2AR$ binding in each assay even though parent COS-7 cells lacked any $α_2AR$ sites. Moxonidine and p-iodoclondine (PIC) were the compounds tested for their affinity to the membranes of transfected cells. As can be seen, the affinities of these compounds in competition with $^{125}PIC$ were well within the high affinity (nM) range.

The following $IC_{50}$ values and Hill slopes were obtained in this study: moxonidine, $IC_{50}=45.1$ nM (Hill slope= 0.35±0.04); p-iodoclonidine without PKC pretreatment of the membranes, $IC_{50}=2.3$ nM (Hill slope=0.42±0.06); p-iodoclonidine with PKC pretreatment of the membranes, $IC_{50}=19.0$ nM (Hill slope=0.48±0.08). Shallow Hill slopes for $[^{125}I]$p-iodoclonidine have been reported before in studies of the interaction of moxonidine and p-iodoclonidine with the human platelet $IR_1$ binding site [Piletz and Sletten, (1993)]. Epinephrine failed to displace any of the $[^{125}I]$p-iodoclonidine binding in the transfected cells, as expected since this is a nonadrenergic imidazoline receptor. Furthermore, in untransfected cells less than 5% of the amount of displaceable binding was observed as for the transfected cells—and this "noise" in the parent cells all appeared to be low affinity (data not shown). These results thus demonstrate the high affinities of two imidazoline compounds, p-iodoclonidine and moxonidine, for the portion of our cloned receptor encoded within EST04033. PKC pretreatment of the membranes had no effect in the transfected COS cells.

It was also observed that the level of the expressed protein, as measured by Western blotting of the transfected cells, was consistent with the level of IR binding that was detected. In other words, a protein band was uniquely detected in the transfected cells, and it was of a density consistent with the amount of radioligand binding. Hence, the present results are in keeping with those expected for an imidazoline receptor. In summary, these data provide direct evidence that the EST04033 clone encodes an imidazoline binding site having high affinities for moxonidine and p-iodoclonidine, which is expected for an IR protein.

EXAMPLE 5

Stable Transfection Methods

Stable transfections can be obtained by subcloning the imidazoline receptor cDNA into a suitable expression vector, e.g., pRc/CMV (Invitrogen, San Diego, Calif.), which can then be used to transform host cells, e.g. CHO and HEK-293 cells, using the Lipofectin reagent (Gibco/BRL, Gaithersburg, Md.) according to the manufacturer's instructions. These two host cell lines can be used to increase the permanence of expression of an instant clone. The inventors have previously ascertained that parent CHO cells lack both alpha$_2$-adrenoceptor and IR binding sites [Piletz et al., *J. Pharm. & Exper. Ther.*, 272: 581–587 (1995)], making them useful for these studies. Twenty-four hours after transfection, cells are split into culture dishes and grown in the presence of 600 μg/ml G418-supplemented complete medium (Gibco/BRL). The medium is changed every 3 days and clones a surviving in G418 are isolated and expanded for further investigation.

EXAMPLE 6

Direct Cloning of More Complete Gene and Other Homologous Human IR

Direct probing of other human genomic and cDNA libraries can be performed by preparing labelled cDNA probes from different subcloned regions of our clone. Commercially available human DNA libraries can be used. Besides the cDNA and genomic libraries we have already screened, another genomic library is EMBL (Clontech), which integrates genomic fragments up to 22 kbp long. It is reasonable to expect that introns may exist within other human IR genes so that only by obtaining overlapping clones can the full-length genes be sequenced. A probe encompassing the 5' end of an instant cDNA is generally useful to obtain the gene promoter region. Clontech's Human PromoterFinder DNA Walking procedure provides a method for "walking" upstream or downstream from cloned sequences such as cDNAs into adjacent genomic DNA.

EXAMPLE 7

Methods for Preparing Antibodies to Imidazoline Receptive Proteins

An instant imidazoline receptive polypeptide can also be used to prepare antibodies immunoreactive therewith. Thus, synthetic peptides (based on deduced amino acid sequences from the DNA) can be generated and used as immunogens. Additionally, transfected cell lines or other manipulations of the DNA sequence of an instant imidazoline receptor can provide a source of purified imidazoline receptor peptides in sufficient quantities for immunization, which can lead to a source of selective antibodies having potential commercial value.

In addition, various kits for assaying imidazoline receptors can be developed that include either such antibodies or the purified imidazoline receptor protein. A purification protocol has already been published for the bovine imidazoline receptor in BAC cells [Wang et al, 1992] and an immunization protocol has also been published [Wang et al., 1993]. These same protocols can be utilized with little if any modification to afford purified human IR protein from transfected cells and to yield selective antibodies thereto.

In order to obtain antibodies to a subject peptide, the peptide may be linked to a suitable soluble carrier to which antibodies are unlikely to be encountered in human serum. Illustrative carriers include bovine serum albumin, keyhole limpet hemocyanin, and the like. The conjugated peptide is injected into a mouse, or other suitable animal, where an immune response is elicited. Monoclonal antibodies can be obtained from hybridomas formed by fusing spleen cells harvested from the animal and myeloma cells [see, e.g., Kohler and Milstein, Nature, 256: 495–497 (1975)].

Once an antibody is prepared (either polyclonal or monoclonal), procedures are well established in the literature, using other proteins, to develop either RIA or ELISA assays [see, e.g., "Radioimmunoassay of Gut Regulatory Peptides; Methods in Laboratory Medicine," Vol. 2, chapters 1 and 2, Praeger Scientific Press, 1982]. In the case of RIA, the purified protein can also be radiolabelled and used as a radioactive antigen tracer.

Currently available methods to assay imidazoline receptors are unsuitable for routine clinical use, and therefore the development of an assay kit in this manner could have significant market appeal. Suitable assay techniques can employ polyclonal or monoclonal antibodies, as has been previously described [U.S. Pat. No. 4,376,110 (issued to David et al.), the disclosure of which is incorporated herein by reference].

SUMMARY

In summary, we have identified unique DNA sequences that have properties expected of a gene and the cDNA transcript(s) of an imidazoline receptor. Prior to our first cloning the cDNA, only two sequences of EST cDNA were identified within public databases having similar nature. But, these were both partial and imprecise sequences—not identified at all with respect to any encoded protein. Indeed, one of them (HSA09H122) was reported to be contaminated. In our hands, the other EST 04033 clone was correctly sequenced for the first time (in its entirety=3318 bp). Prior to this, even the size of EST 04033 was unknown. The present inventors also demonstrated that an imidazoline receptive site can be expressed in cells transfected with the EST 04033 cDNA clone, and this site has the proper potencies of an IR. We have deduced most of the complete cDNA encoding this protein.

The present invention has been described with reference to specific examples for purposes of clarity and explanation. Certain obvious modifications of the invention readily apparent to one skilled in the art can be practiced within the scope of the appended claims.

What is claimed is:

1. An isolated polypeptide including a site which is receptive to imidazoline compounds, said polypeptide containing an amino acid sequence shown in SEQ ID NO: 5.

2. A polypeptide as defined in claim 1, having a molecular weight of about 50 to 80 kDa.

3. A polypeptide as defined in claim 2, having a molecular weight of about 70 kDa.

4. A polypeptide of claim 1, which is immunoreactive with at least one of Reis antiserum and Dontenwill antiserum.

5. A polypeptide of claim 1, which is a human polypeptide.

6. A fragment of the amino acid sequence shown in SEQ ID NO:5, which fragment is receptive to imidazoline compounds.

* * * * *